(12) United States Patent
Shoichet et al.

(10) Patent No.: US 11,213,490 B2
(45) Date of Patent: Jan. 4, 2022

(54) ENCAPSULATION-FREE CONTROLLED PROTEIN RELEASE SYSTEM

(71) Applicant: Molly Shoichet, Toronto (CA)

(72) Inventors: Molly Shoichet, Toronto (CA);
Malgosia M. Pakulska, Toronto (CA);
Irja Elliott Donaghue, Whitby (CA);
Jaclyn M. Obermeyer, Toronto (CA)

(73) Assignee: Molly Shoichet, Toronto (CA)

( * ) Notice: Subject to any disclaimer, the term of this patent is extended or adjusted under 35 U.S.C. 154(b) by 0 days.

(21) Appl. No.: 16/097,916

(22) PCT Filed: May 19, 2017

(86) PCT No.: PCT/CA2017/050615
§ 371 (c)(1),
(2) Date: Oct. 31, 2018

(87) PCT Pub. No.: WO2018/000082
PCT Pub. Date: Jan. 4, 2018

(65) Prior Publication Data
US 2019/0125691 A1 May 2, 2019

Related U.S. Application Data

(60) Provisional application No. 62/338,694, filed on May 19, 2016.

(51) Int. Cl.
| | |
|---|---|
| *A61K 9/51* | (2006.01) |
| *A61K 9/06* | (2006.01) |
| *A61K 9/14* | (2006.01) |
| *A61K 38/18* | (2006.01) |
| *A61K 38/19* | (2006.01) |
| *A61K 47/36* | (2006.01) |
| *A61K 47/38* | (2006.01) |
| *A61K 38/00* | (2006.01) |

(52) U.S. Cl.
CPC ............. *A61K 9/5153* (2013.01); *A61K 9/06* (2013.01); *A61K 9/146* (2013.01); *A61K 38/185* (2013.01); *A61K 38/1816* (2013.01); *A61K 38/195* (2013.01); *A61K 47/36* (2013.01); *A61K 47/38* (2013.01); *A61K 38/00* (2013.01)

(58) Field of Classification Search
CPC .......................... A61K 47/6903; A61K 9/5153
See application file for complete search history.

(56) References Cited

U.S. PATENT DOCUMENTS

| | | | |
|---|---|---|---|
| 6,632,457 B1 * | 10/2003 | Sawhney | A61K 9/1647 424/486 |
| 9,238,008 B2 * | 1/2016 | Brakenhielm | A61K 9/5036 |
| 2008/0267876 A1 * | 10/2008 | Benita | A61K 9/167 424/9.1 |
| 2013/0196915 A1 * | 8/2013 | Wang | A61K 47/6903 514/11.4 |

OTHER PUBLICATIONS

I. Elliott Donaghue, C. H. Tator, and M. S. Shoichet, "Sustained delivery of bioactive neurotrophin-3 to the injured spinal cord," Biomater. Sci., vol. 3, pp. 65-72, 2015.
M. M. Pakulska, K. Vulic, R. Y. Tam, and M. S. Shoichet, "Hybrid Crosslinked Methylcellulose Hydrogel: A Predictable and Tunable Platform for Local Drug Delivery.," Adv. Mater., Jul. 2015.
O. A. Hickey, J.-F. Mercier, M. G. Gauthier, F. Tessier, S. Bekhechi, and G. W. Slater, "Effective molecular diffusion coefficient in a two-phase gel medium.," J. Chem. Phys., vol. 124, No. 20, p. 204903, May 2006.
A. Tuladhar, C. M. Morshead, and M. S. Shoichet, "Circumventing the blood—brain barrier☐: Local delivery of cyclosporin A stimulates stem cells in stroke-injured rat brain," J. Control. Release, vol. 215, pp. 1-11, 2015.
M. Singh, J. Kazzaz, J. Chesko, E. Soenawan, M. Ugozzoli, M. Giuliani, M. Pizza, R. Rappouli, and D. T. O' Hagan, "Anionic Microparticles are a Potent Delivery System for Recombinant Antigens from Neisseria meningitidis Serotype B," J. Pharm. Sci., vol. 93, No. 2, pp. 273-282, 2004.
S. K. Sahoo, J. Panyam, S. Prabha, and V. Labhasetwar, "Residual polyvinyl alcohol associated with poly (D,L-lactide-co-glycolide) nanoparticles affects their physical properties and cellular uptake," J. Control. Release, vol. 82, No. 1, pp. 105-114, 2002.
Y. Liu and S. P. Schwendeman, "Mapping microclimate pH distribution inside protein-encapsulated PLGA microspheres using confocal laser scanning microscopy," Mol. Pharm., vol. 9, No. 5, pp. 1342-1350, 2012.
Y. Wang, M. J. Cooke, N. Sachewsky, C. M. Morshead, and M. S. Shoichet, "Bioengineered sequential growth factor delivery stimulates brain tissue regeneration after stroke," J. Control. Release, vol. 172, No. 1, pp. 1-11, 2013.
C. Géral, A. Angelova, and S. Lesieur, "From Molecular to Nanotechnology Strategies for Delivery of Neurotrophins: Emphasis on Brain-Derived Neurotrophic Factor (BDNF)," Pharmaceutics, vol. 5, No. 1, pp. 127-167, Feb. 2013.

(Continued)

*Primary Examiner* — Kyle A Purdy
(74) *Attorney, Agent, or Firm* — Hill & Schumacher

(57) ABSTRACT

The present disclosure provides a delivery system for controlled protein release without encapsulation. Identical, burst-free, extended release profiles for three different protein therapeutics were obtained with and without encapsulation in PLGA nanoparticles embedded within a hydrogel. Using both positively and negatively charged proteins, it was shown that short-range electrostatic interactions between the proteins and the PLGA nanoparticles are the underlying mechanism for controlled release. Moreover, tunable release was demonstrated by modifying nanoparticle concentration, nanoparticle size, or environmental pH. Additionally, the utility of this system was demonstrated in vivo for BDNF delivery in a rat model of stroke. These new insights obviate the need for encapsulation and offer promising, translatable strategies for more effective delivery of therapeutic biomolecules.

29 Claims, 15 Drawing Sheets

(56) References Cited

OTHER PUBLICATIONS

M. M. Pakulska et al., "Encapsulation-free controlled release: Electrostatic adsorption eliminates the need for protein encapsulation in PLGA nanoparticles"; Sci. Adv.; pp. 1-10; May 27, 2016.
J.C. Stanwick et al ; "Enhanced neurotrophin-3 bioactivity and release from a nanoparticle-loaded composite hydrogel"; Journal of Controlled Release, 2012, 160, pp. 666-675.
N. K. Singh et al.; "Nanostructure controlled sustained delivery of human growth hormone using injectable biodegradable, pH/temperature responsive nanobiohybrid 7, pp. 3043-3054. hydrogel", Nanoscale, 2015.
S. Gunasekaran et al.; "Use of whey protein for encapsulation and controlled delivery applications"; Journal of Food Engineering, 2007, 83, pp. 31-40.
H. Zhang et al.; "New progress and prospects: The application of nanogel in drug delivery"; Materials Science and Engineering C; 2016, C60, pp. 560-568.
International Search report PCT/CA2017/050615 dated Jan. 11, 2018.

\* cited by examiner

A. Contralesional

B. Ipsilesional

ENCAPSULATION-FREE CONTROLLED PROTEIN RELEASE SYSTEM

FIELD

The present disclosure relates to a biocompatible composite delivery system for encapsulation-free controlled therapeutic protein delivery, long term release from the delivery system, and method for making the delivery system.

BACKGROUND

Controlled protein release is a key strategy to reduce both the systemic side effects associated with high therapeutic protein concentrations and the frequency of therapeutic protein administration. One of the most widely studied methods of controlling protein release is encapsulation within a polymeric matrix such as poly(lactic-co-glycolic acid) (PLGA, also known as poly(lactide-co-glycolide)), poly(lactic acid) (PLA), poly(glycolic acid) (PGA), poly (ortho esters), poly(anhydrides), poly(amides), poly(ester amides), poly(phosphoesters), poly(ε-caprolactone) (PCL), poly(alkyl-cyanoacrylate), poly(ethylene glycol) (PEG), chitosan, hyaluronic acid, or gelatin, which slows diffusion. For example, PLGA is widely used for encapsulation due to its biocompatibility, biodegradability, wide range of degradation rates, and long clinical history.

PLGA is typically formulated into injectable, protein-containing micro- or nanoparticles by double emulsion solvent evaporation, phase separation, or spray drying techniques. All of these methods involve organic solvents, high shear forces, and/or high temperatures that result in protein denaturation and aggregation. In addition, PLGA protein formulations often suffer from low encapsulation efficiency and low protein loading. The modification of process parameters such as solvent type, volume, or co-encapsulation with various excipients such as PEG, sugars, or bases can improve encapsulation efficiency and protein stability. Embedding protein-loaded PLGA nanoparticles within a hydrogel enables their localization at the site of hydrogel injection and is known to reduce the initial burst and extend the release of encapsulated proteins, yet the requirement for encapsulation in order to achieve sustained release remains unchanged.

The use of PLGA nanoparticles for drug delivery using surface adsorption has been studied (Cai et al., 2008; Singh et al., 2004), but these systems do not incorporate a hydrogel and exhibit significant burst release and short release times (<1 d).

Long term delivery of protein therapeutics is required in numerous chronic disease or injury treatments, including, for example, insulin for diabetes treatment; antibodies against vascular endothelial growth factor (anti-VEGF) for treatment of age-related macular degeneration; neurotrophins for axon regeneration following central nervous system injury; enzyme replacement therapies; cytokine delivery for immune modulation or anti-cancer treatment; growth/differentiation factors to promote stem cell differentiation, proliferation, and survival after transplant in regenerative medicine and tissue engineering applications. Therapeutic proteins may also include hormones, protein vaccines, and fusion proteins.

Therefore it would be very advantageous to provide a delivery system for low-burst, controlled therapeutic protein delivery with long term release without subjecting the protein to harsh processing conditions.

SUMMARY OF THE INVENTION

The present invention provides a biocompatible composite delivery system composed of a hydrogel, polymer nanoparticles, and proteins. This system shows controlled, encapsulation-free protein delivery and long term release, with low initial burst release, due to short range electrostatic interactions between the particles and protein. The method for synthesizing the composite delivery system is also provided.

In an embodiment there is disclosed a biocompatible polymer composite comprised of a hydrogel, proteins and nanoparticles for controlled protein release, said proteins are not encapsulated by said nanoparticles and interact with said nanoparticles by short-range interactions, characterized in that said biocompatible polymer composite yields an extended protein release profile on the order of weeks, and the extended protein release is caused by the short-range interactions between said proteins and nanoparticles.

Also disclosed is a process for producing a drug delivery system for extended protein release which comprises
selecting a protein to be released over an extended period of time;
selecting a nanoparticle on the basis that it is made of a polymer-based material which has a charge complimentary to the charge on the protein such that the nanoparticle and the protein interact by electrostatic interactions
producing the nanoparticles separate from the protein; and
mixing the protein and separate nanoparticles together with a hydrogel material under conditions conducive to the hydrogel forming to encapsulate the nanoparticles and the protein.

There is also disclosed a method for providing controlled release of a protein, the method comprising:
selecting a protein to be released over an extended period of time;
selecting a nanoparticle on the basis that it is made of a polymer-based material which has a charge complimentary to the charge on the protein such that the nanoparticle and the protein interact by electrostatic interactions
producing the nanoparticles separate from the protein;
mixing the protein and separate nanoparticles together with a hydrogel material under conditions conducive to the hydrogel forming to encapsulate the nanoparticles and the protein to produce a biocompatible polymer composite; and
depositing the biocompatible polymer composite into an environment, whereupon degradation of the biocompatible polymer composite is characterized in that said biocompatible polymer composite yields an extended protein release profile on the order of weeks, and the extended protein release is caused by the short-range interactions between said proteins and nanoparticles.

The hydrogel may comprise any one of agarose, carrageenan, collagen, chitosan, alginate, gelatin, fibrin, hyaluronan, methyl cellulose, poly(ethylene glycol), poly(ethylene oxide), dextran, poly(vinyl alcohol), polypeptides, poly(N-isopropylacrylamide), poly(caprolactone), poly(urethane), poly(propylene oxide), poly(lactide-co-glycolic acid), poly (acrylates) and derivatives, co-polymers and physicals blends thereof The nanoparticles may be comprised of: poly(lactide-co-glycolide), poly(lactic acid), poly(glycolic acid), poly(ortho esters), poly(anhydrides), poly(amides), poly(ester amides), poly(phosphoesters), poly(ε-caprolactone), poly(alkyl-cyanoacrylate), poly(ethylene glycol), chitosan, hyaluronic acid, gelatin, or derivatives or co-polymers or physicals blends thereof.

The proteins may be therapeutically relevant proteins for the treatment of disease, disorder, or regenerative medicine applications.

The protein may be a growth factor, differentiation factor, antibody, chemokine, cytokine, hormone, protein vaccine, enzyme or fusion protein.

The protein may be any one of nerve growth factor (NGF), erythropoietin (EPO), fibroblast growth factor (FGF), insulin-like growth factor (IGF), glial-derived neurotrophic factor (GDNF), epidermal growth factor (EGF), ciliary neurotrophic factor (CNTF), bone morphogenic protein (BMP), vascular endothelial growth factor (VEGF), stromal cell-derived factor (SDF), neurotrophin 3 (NT-3), brain-derived neurotrophic factor (BDNF), platelet-derived growth factor (PDGF), epidermal growth factor (EGF), hepatocyte growth factor (HGF), adrenomedulin (AM), angiopoietin (Ang), autocrine motility factor, leukemia inhibitory factor (LIF), interleukin-6 (IL-6), colony-stimulating factors, ephrins, fetal bovine somatotrphin (FBS), growth differentiation factor-9 (GDF9), hepatoma-derived growth factor (HDGF), insulin, interleukins, keratinocyte growth factor (KGF), migration-stimulating factor (MSF), myostatin (GDF-8), neuroregulins, placental growth factor (PGF), renalase (RNLS), T-cell growth factor (TCGF), thrombopoietin (TPO), transforming growth factors, enzymes, or antibodies.

The short-range interactions may occur between positively charged proteins and negatively charged particles in a neutral pH environment. In which protein release is initiated as the negatively charged particles degrade into products that decrease the strength of said short-range interactions between positively charged proteins and negatively charged particles.

Alternatively short-range interactions may occur between negatively charged proteins and positively charged particles in a neutral pH environment in which protein release is initiated as the positively charged particles degrade into products that decrease the strength of said short-range interactions between negatively charged proteins and positively charged particles.

The nanoparticles may have a diameter in a range from about 1 to 1000 nm and in some embodiments the nanoparticles may have a diameter in a range from about 100 to 1000 nm.

The biocompatible polymer composite may have a composition of 0.1 to 20 wt % hydrogel/polymer scaffold, 10 pg/mL to 20 mg/mL protein and 0.1 to 20 wt % nanoparticles.

A further understanding of the functional and advantageous aspects of the disclosure can be realized by reference to the following detailed description and drawings.

BRIEF DESCRIPTION OF THE DRAWINGS

Embodiments of the invention will now be described, by way of example only, with reference to the drawings, in which:

FIG. 8B(ii) shows the release of 0.5, 1, or 10 μg of NT-3 from composite HAMC with 10 wt % PLGA nanoparticles. The concentration of NT-3 incorporated can be increased up to 20× with virtually no change in release profile. Cumulative percent of NT-3 released is significantly higher for 10 μg compared to 1 μg and 0.5 μg at 10d and 14d (p>0.05) and significantly lower for 0.5 μg compared to 1 μg and 10 μg at 21d and 28d (p>0.05). (n=3 for all releases, mean±standard deviation plotted).

FIG. 18A shows significant increases in synaptophysin expression in BDNF-treated animals relative to injury-only and vehicle-treated animals in contralesional hemisphere regions of interest R1 and R2 (n=3, mean±standard deviation plotted, $p^* \leq 0.05$).

FIG. 18B shows a significant decrease in synaptophysin expression in injury-only animals relative to vehicle-treated animals in the ipsilesional hemisphere (n=3, mean±standard deviation plotted, $p^* \leq 0.05$).

DETAILED DESCRIPTION OF THE INVENTION

Figure 1:
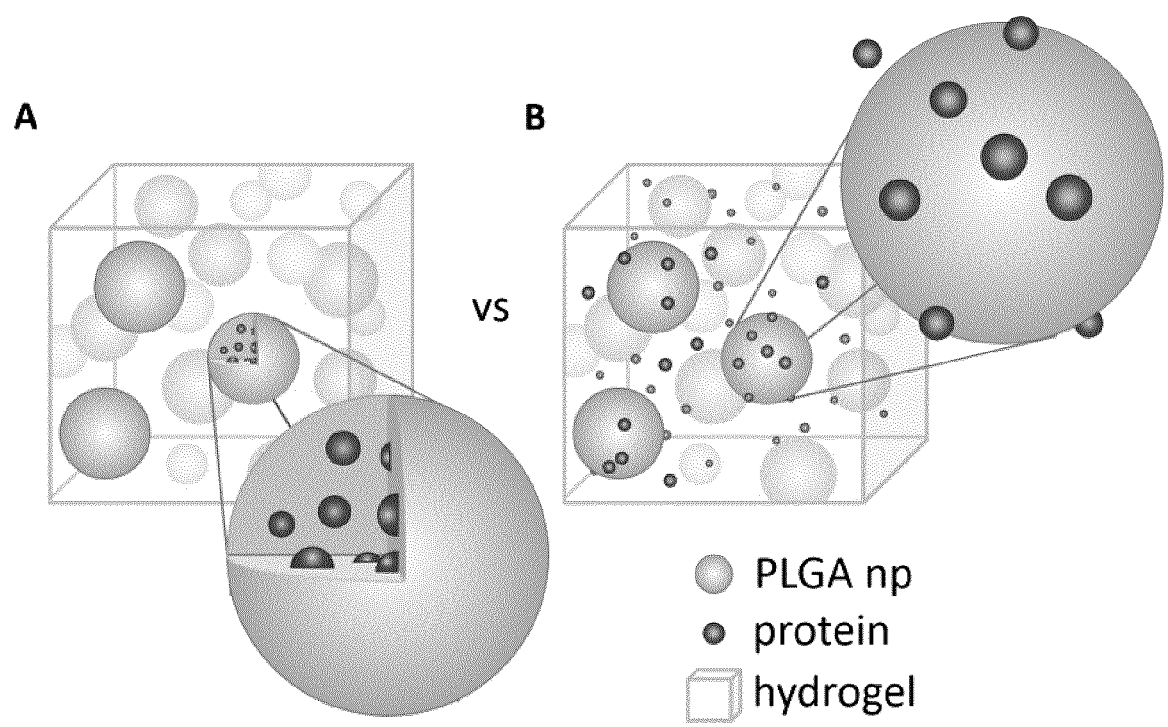
FIG. 1A shows a PLGA nanoparticle system where protein is encapsulated in a PLGA nanoparticle dispersed in a hydrogel.
FIG. 1B shows a PLGA nanoparticle system where protein and blank PLGA nanoparticles are dispersed in a hydrogel. Protein adsorbs to the PLGA nanoparticles, but is not encapsulated within them.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to a delivery system for encapsulation-free controlled protein delivery and long term release from the delivery system, and method for making the delivery system.

As used herein, the term "about", when used in conjunction with ranges of dimensions, temperatures, concentrations or other physical properties or characteristics is meant to cover slight variations that may exist in the upper and lower limits of the ranges of dimensions so as to not exclude embodiments where on average most of the dimensions are satisfied but where statistically dimensions may exist outside this region.

As used herein, "hydrogels" refer to materials that are formed by crosslinking polymer chains, through physical, ionic or covalent interactions and are known for their ability to absorb water.

Physical interactions also include: hydrophobic interactions between polymer chains that lead to gelation with increased temperature; hydrogen bonding or other non-covalent interactions that result in gelation with decreased temperature; reduced solubility and fibrillation that result in gelation with increased pH; among other non-covalent interactions. Hydrogels characterized by crosslinking that are produced through ionic or covalent interactions may require a crosslinking (XL) agent and/or an initiator and activation by methods such as heat or radiation. Hydrogels can be fabricated with varying degrees of porosity (or network density), stiffness, swelling, and gelation properties.

Embodiments of hydrogels used herein are comprised of high water content polymers. Hydrogels suitable for drug delivery applications may be composed of naturally-derived or synthetic polymers that include, but are not limited to: agarose, carrageenan, collagen, chitosan, alginate, gelatin, fibrin, hyaluronan, methyl cellulose, dextran, poly(ethylene glycol), poly(ethylene oxide), poly(vinyl alcohol), polypeptides, poly(N-isopropylacrylamide), poly(caprolactone), poly(urethane), poly(propylene oxide), poly(lactide-co-glycolic acid), or derivatives or co-polymers or physicals blends thereof As used herein, the terms nanoparticles, nanospheres, microparticles and microspheres are used interchangeably. While nanoparticles and nanospheres are typically submicron in diameter and microspheres and microparticles are typically above 1 micron in diameter, the two sizes are used for controlled delivery of proteins and drugs. The terms (nano/micro)particles and (nano/micro)spheres are used interchangeably in the literature. Particles include spherical shaped particles but are not limited to this shape. Particles can be composed of polymers that include, but are not limited to: poly(lactide-co-glycolide), poly(lactic acid), poly (glycolic acid), poly(ortho esters), poly(anhydrides), poly (amides), poly(ester amides), poly(phosphoesters), poly(ε-caprolactone), poly(alkyl-cyanoacrylate), poly(ethylene glycol), chitosan, hyaluronic acid, gelatin, dextran, derivatives thereof, co-polymers thereof, physicals blends thereof or polymeric coatings thereof on other polymeric or inorganic particles.

As used herein, a "short range interaction" refers to an electrostatic interaction between two species but may also include contributions from any non-covalent interaction including Van der Waals, hydrophobic, electrostatic, hydrogen bonding, or ionic.

As used herein, "burst release" refers to rapid release of the protein within the first 1 to 3 days, before the onset of polymer degradation. "Low burst release" as used herein refers to a burst release of less than 20% of the total amount of protein released.

As used herein, "long term release" refers to sustained release of protein for a period greater than 2 weeks.

As used herein, a "delay" in release refers to a period of time at the beginning of the release period during which there is less than 10% cumulative release for at least 2 days.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

It is known to those skilled in the art that embedding PLGA nanoparticles within a hydrogel enables their localization at the site of hydrogel injection and is known to reduce the initial burst and extend the release of encapsulated proteins. The present disclosure is based on the surprising discovery, made while studying the release of three growth factors relevant to central nervous system (CNS) repair strategies, that the release profiles measured for each of them were independent of encapsulation of the growth factors within PLGA nanoparticles. The three growth factors for which this surprising observation was made are stromal cell-derived factor (SDF1α hereafter referred to as simply SDF), neurotrophin 3 (NT-3), and brain-derived neurotrophic factor (BDNF).

Sustained, burst-free release profiles were obtained whether the proteins were encapsulated in PLGA nanoparticles that were then dispersed within a hydrogel (FIG. 1A) or simply mixed into the identical hydrogel with blank PLGA nanoparticles (FIG. 1B). FIG. 1A (10) shows a protein encapsulated by a PLGA nanoparticle (12), embedded in a hydrogel (14). In FIG. 1B an un-encapsulated protein is shown at 16, adsorbed to the surface of a blank PLGA nanoparticle at 18.

To the best of the inventors' knowledge, this is the first example of PLGA nanoparticles being used for long-term, controlled release without encapsulation.

Without being limited to any theory, the inventors hypothesize that adsorption due to short-range electrostatic interactions between the proteins and the PLGA nanoparticles are the governing factor for release in this system and tested this hypothesis by controlling the release through nanoparticle concentration, nanoparticle size, and pH. The studies discussed hereinafter were carried out in an attempt to elucidate the mechanism involved in the binding and subsequent release of the proteins to the outer surface of the nanoparticles, and to understand the beneficial lack of initial burst release and long term release, up to several weeks. To substantiate the data, Monte Carlo simulations were performed based on this release mechanism hypothesis and obtained similar release profiles.

Materials and Methods

PLGA was purchased from Sigma-Aldrich (50:50 lactide: glycolide, carboxy terminated, MW 7-17 kDa) or Lactel Absorbable Polymers, Durect Corporation (50:50 lactide: glycolide, carboxy terminated, 0.15-0.25 dL/g in HFIP). Proteins were sourced as follows: SDF1α (R&D Systems), NT-3, (Peprotech, Rocky Hill USA), BDNF (Peprotech), EPO (Janssen). ELISA kits were purchased from R&D Systems for SDF and NT-3 and Promega for BDNF. All other materials were obtained as indicated.

PLGA Nanoparticle Formation

PLGA nanoparticles were formed by water/oil/water double emulsion-solvent evaporation as previously described. Briefly, 120 mg of PLGA and 0.05% Pluronic® NF-127 (BASF, Mississauga Canada) were dissolved in 900 µl dichloromethane (DCM) (Caledon Labs, Georgetown Canada) and vortexed with 100 µl of 120 mg/mL bovine serum albumin (BSA) (Sigma Aldrich) in artificial cerebrospinal fluid (aCSF) (149 mM NaCl, 3 mM KCl, 0.8 mM $MgCl_2$, 1.4 mM $CaCl_2$, 1.5 mM $Na_2HPO_4$, 0.2 mM $NaH_2PO_4$, pH 7.4) to achieve 10% w/w BSA/PLGA in the final formulation. The mixture was then sonicated for 2 minutes on ice. To encapsulate SDF, NT-3, BDNF, or EPO, these proteins were dissolved in the aqueous phase prior to sonication. The primary emulsion was then added to 3 mL of a 2.5% w/v solution of poly(vinyl alcohol), (PVA) (30-70 kg/mol, Sigma Aldrich), vortexed, and sonicated for 2 minutes on ice. This secondary emulsion was added to a hardening bath of PVA and stirred for a minimum of 4 h to allow the DCM to evaporate. The resultant nanoparticles were washed four times by ultracentrifugation, lyophilized, and stored at −20° C. Nanoparticles were sized by dynamic light scattering (DLS, Malvern Instruments, Montreal Canada). For 1000 nm nanoparticles, the volume of PVA added in the secondary emulsion was increased to 5 mL.

Measurement of Encapsulation Efficiency

SDF1α

Encapsulation efficiency was measured by dissolving 10 mg of dry protein-loaded PLGA nanoparticles in 1 mL dimethyl sulfoxide (DMSO) for 1 hour at 37° C. 10 mL of 0.05M NaOH containing 0.5% w/v sodium dodecyl sulfate (SDS) was then added and the sample left for another hour at room temperature on a rocker. SDF1α concentration was then measured by ELISA at a 1:10 dilution as directed.

BDNF/NT-3

Encapsulation efficiency was measured by dissolving 5 mg of dry protein-loaded PLGA nanoparticles in 5 mL of 0.05 M NaOH on a shaker at room temperature for 30 minutes. The protein concentration was determined by ELISA.

Preparation of PLGA Nanoparticles/Hydrogel DDS

Composite HAMC

To form the HAMC hydrogel, methyl cellulose (MC, 300 kg/mol, Shin-Etsu, Tokyo Japan) and sodium hyaluronate (HA, 1.4-1.8×10$^6$ g/mol, NovaMatrix, Sandvika Norway) were dissolved in aCSF using a dual asymmetric centrifugal mixer (Flacktek, Landrum USA) to a final concentration of 2.8% w/v HA and 6% w/v MC. Nanoparticles were dispersed in aCSF at 20% w/w by 5 min of bath sonication and protein (NT-3, BDNF, or EPO) was then added. Composite HAMC was formed by blending the nanoparticle dispersion and HAMC at a 1:1 ratio using a dual asymmetric centrifugal mixer.

Composite XMC

XMC was prepared as previously described [Pakulska, Adv. Mat., 2015] except empty PLGA nanoparticles dispersed in aCSF and SDF were added prior to mixing in the crosslinker.

Composite Agarose

Ultralow gelling temperature SeaPrep™ Agarose (Lonza) was dissolved in aCSF to a concentration of 3% w/v by microwaving on high power in 4-second bursts and vortexing until clear. The solution was allowed to cool to room temperature before further handling. Nanoparticles were dispersed in aCSF at 20% w/w by 5 min of bath sonication and BDNF was then added. Room temperature agarose was added to the nanoparticle dispersion at a 1:1 v/v ratio and a dual asymmetric centrifugal mixer was used to create the composite agarose. 100 µl of composite agarose was pipetted into a 2 mL centrifuge tube and allowed to gel at 4° C. for 1 hour.

In Vitro Release Assays

Composite HAMC/XMC

100 µl of either HAMC, XMC, composite HAMC, or composite XMC with or without dispersed protein was injected into a 2 mL centrifuge tube. After 10 min of gelation at 37° C., 900 µl (for release of BDNF, NT-3) or 400 µl (for release of SDF) of pre-warmed aCSF was added. For BDNF releases the aCSF also contained 0.1% w/v BSA to ensure sustained bioactivity. The supernatant was completely replaced at designated time points for the duration of the release study, and the protein concentration was assessed by the relevant ELISA. At the conclusion of the study, the remaining gel was processed as described above for encapsulation efficiency and the protein remaining was quantified by ELISA. Releases were performed in triplicate. For release of SDF at different pH, the pH of the aCSF was adjusted to pH 5 or pH 3 used in both the gel formation and the supernatant.

Agarose/Agarose with High Salt

Agarose or agarose composite with or without dispersed BDNF, previously prepared in a 2 ml centrifuge tube, was placed in an incubator at 37° C. to warm for 10 minutes. 900 µl of pre-warmed aCSF (0.1% w/v BSA) was added to the composite, and this supernatant was completely replaced at designated time points for the duration of the release study. For the high salt agarose composite, aCSF with 0.5 M NaCl was used to create the gel and the release supernatant. At the end of the study, 0.5 ml of 0.5 M NaCl was added to the gel to release any remaining BDNF. ELISA was used to determine BDNF concentration at each time point and the BDNF remaining in the gel. Releases were performed in triplicate.

Adsorption Study

2 µg of BDNF was mixed with 20 mg of PLGA nanoparticles in 200 µl of aCSF and incubated for 0 (as fast as possible), 10, and 60 minutes at 37° C. At each designated timepoint, the mixture was centrifuged at 12,000 rpm for 2 minutes to pellet the nanoparticles. The supernatant was carefully removed and analyzed by ELISA. Controls of soluble BDNF in aCSF with no nanoparticles were processed in the same way at each time point to take into account any losses due to centrifugation or adsorption to the tube. Samples of PLGA nanoparticles in aCSF with no BDNF were used as blanks for the ELISA. The amount of BDNF adsorbed to the nanoparticles was calculated as 2 µg minus the amount detected in the supernatant. Each time point was performed in triplicate.

Bioactivity Assays

All animal procedures were performed in accordance with the Guide to the Care and Use of Experimental Animals (Canadian Council on Animal Care) and protocols were approved by the Animal Care Committee at the University of Toronto.

NT-3—Dorsal Root Ganglion Explant Assay

The bioactivity of released NT-3 was quantified as previously described [1]. Sprague-Dawley rat embryo dorsal root ganglion (DRG, E17) were harvested and pooled in neural basal media containing 1 vol % fetal bovine serum, 2 vol % B-27® serum-free supplement, 1 vol % penicillin-streptomycin, and 1 vol % $_L$-glutamine. The DRG were placed on glass coverslips (12 mm diameter) coated with poly-D-lysine (50 µg/mL in sterile water) and laminin (5 µg/mL in PBS) in a 24-well plate. Media with aCSF alone (control media), media with soluble (standard) NT-3, or media with released NT-3 was added to each well. The DRG were fixed after 48 h incubation in 4% paraformaldehyde and stained with NF200 and DAPI (Sigma Aldrich). DRG were imaged on an Olympus FV1000 confocal microscope. Image analysis was performed with ImageJ (National Institutes of Health). For each DRG, the DAPI+ area of the multicellular DRG body was subtracted from the total NF200+ area (centre+extended neurites) to yield the area of neurite outgrowth. A minimum of 3 DRGs were assayed per group.

SDF—Neurosphere Migration Assay

In vitro activity of SDF was quantified as described previously [2]. Briefly 125 μl of SDF release samples or controls were diluted to 2000 ng/mL (or as high as possible) in serum-free media and adjusted to pH 7. Each was then added to 125 μl of adult rat spinal cord neurosphere suspension in a fibronectin coated 48-well tissue culture plate. Neurospheres were allowed to adhere for 1 hour in a tissue culture incubator at 37° C., 5% $CO_2$. Images were collected of four neurospheres per well using an inverted Olympus laser scanning confocal microscope with automated stage at 10× magnification. The coordinates of each image were saved. The plate was then returned to the incubator. Using the saved coordinates, the same neurospheres were imaged again 24 hours later. Images were analyzed using ImageJ (National Institutes of Health). The initial area of the neurosphere (A1) as well as the final area of cells migrated out from the neurosphere (A2) were measured and subtracted to yield the total area of migration (A2−A1).

BDNF—Dorsal Root Ganglion Neurite Outgrowth Assay

In vitro activity of BDNF was determined using a DRG bioassay. Rat embryo DRG (E17 female Sprague-Dawley rats, n=3) were removed and pooled in media composed of neural basal media supplemented with 2% B-27® serum-free supplement, 1% penicillin-streptomycin, and 1% L-glutamine (Life Technologies). The DRG were then placed on 12 mm diameter glass coverslips coated with poly-D-lysine (50 μg/mL) and laminin (5 μg/mL) in a 24-well plate. Each release sample replicate was tested on a separate plate. All wells contained 3 DRG and were treated with 0.5 mL of media and 0.5 mL of the BDNF release study supernatant (7, 28, 35, and 42 d). For the controls, 0.5 mL media and 0.5 mL of aCSF (without BDNF) was added to the wells. The DRG were grown for 48 h at 37° C. and 5% CO2, fixed with 4% paraformaldehyde (PFA) and processed for immunocytochemistry. The DRG were imaged using an inverted confocal laser scanning microscope (Olympus FV1000). Neurite outgrowth area was calculated by subtracting the cell body area from the total area of the DRG neurite outgrowth. To account for any differences in cell body size the neurite outgrowth area was standardized to the cell body area for statistical analysis. Neurite outgrowth of DRG treated with release samples was compared to controls to assess bioactivity.

Transmission Electron Microscopy

PLGA nanoparticles were suspended in water at 2 mg/mL with sonication for 5 min. Sample (5 μL) was deposited onto a freshly glow-discharged 400 mesh carbon coated copper transmission electron microscopy (TEM) grid (Ted Pella, Inc.) and allowed to adhere for 4 min. Excess liquid was removed with filter paper and nanoparticles then stained with 1% ammonium molybdate (AM, w/v, 5 μL, pH 7.0, 30 s) or 2% uranyl acetate (UA, w/v, 5 μL, pH 4.3, 15 seconds). Stain was wicked away with filter paper and samples immediately imaged using a Hitachi H-7000 microscope operating at 75 kV. Images were captured using an Advanced Microscopy Techniques (AMT) XR-60 CCD camera with typical magnifications between 30000-75000×.

Zeta Potential Measurements

PLGA nanoparticles were suspended at 0.1 mg/mL in distilled water with 1 mM KCl. Zeta potential was measured in a disposable folded capillary cell using a Zetasizer® Nano ZS (Malvern).

Swelling Study

An in vitro swelling study was performed as previously described [2]. Briefly, 180 μL of HAMC or composite HAMC was injected into a 2 mL centrifuge tube. After incubation at 37° C. for 10 min, 1620 μL of pre-warmed aCSF was added. At each timepoint, the tube was weighed after complete removal of the aCSF. The normalized swelling ratio, Q, was determined by the following equation:

$$Q_t = \frac{m_t - m_{tube}}{m_0 - m_{tube}}$$

where $m_t$ is the total mass at each timepoint, $m_0$ is the total mass at time zero, and $m_{tube}$ is the mass of the centrifuge tube.

Monte Carlo Modeling

The on-lattice Monte Carlo simulations model proteins as non-interacting point-particles stochastically diffusing on a cubic lattice of size a, representing the hydrogel, with an effective diffusion coefficient [3]. Proteins that diffuse to the edge of the cubic simulation box permanently escape the hydrogel. To determine the Monte Carlo time step, $T_{MC}$, in hours for a set of simulations of a hydrogel of size L, a simulation is run in the absence of PLGA nanoparticles and the rapid diffusional release rate is matched to the experimental cumulative release. For L=100a, the conversion (0.0148±0.0001) hrs/$T_{MC}$ is found.

To simulate embedded PLGA nanoparticles, we introduce a number of impenetrable obstacle lattice sites that exclude proteins. Each randomly-placed, non-overlapping nanoparticle (labelled i) is cubic with a hard-core size 2R+a. In addition to the hard-core, each nanoparticle interacts with the proteins through a double step-function potential. Immediately adjacent to the core is a deep attractive potential well of depth $u_i(t)$ per thermal energy and range a. Large negative values of $u_i(t)$ cause proteins to be tightly bound to nanoparticles. In addition, there is a repulsive step-potential height $\varepsilon_i(t)$ per thermal energy and of range a, which represents the barrier to adhesion.

Adsorption is modeled via a simple Metropolis algorithm. To simulate a decrease in attraction due to PLGA hydrolysis, the potentials approach zero after long times as $$u_i(t) = \left(1 - \frac{cN_i(t)}{K}\right) u_0 \text{ and } \varepsilon_i(t) = \left(1 - \frac{cN_i(t)}{K}\right) \varepsilon_0,$$

where c is the number density of nanoparticles, K is the nanoparticle-hydrogel degradation-product carrying capacity per hydrogel volume, and $N_i(t)$ is the stochastically increasing number of degradation products. The number of degradation products grows randomly via an algorithm that reproduces logistic-population statistics $$\frac{dN_i}{dt} = r_0 N_i(t) \left[1 - \frac{\sum N_i(t)}{KL^3}\right],$$

where the summation occurs over all nanoparticles in the hydrogel and $r_0$ represents the first-order PLGA degradation rate constant. This captures the increase in the degradation rate due to the increase in acidic degradation products over time (self-catalyzed PLGA degradation), while limiting the degradation rate by the degradation-product carrying capacity. The free simulation parameters are $r_0$, K, $u_0$, and $\varepsilon_0$.

Figure 2:
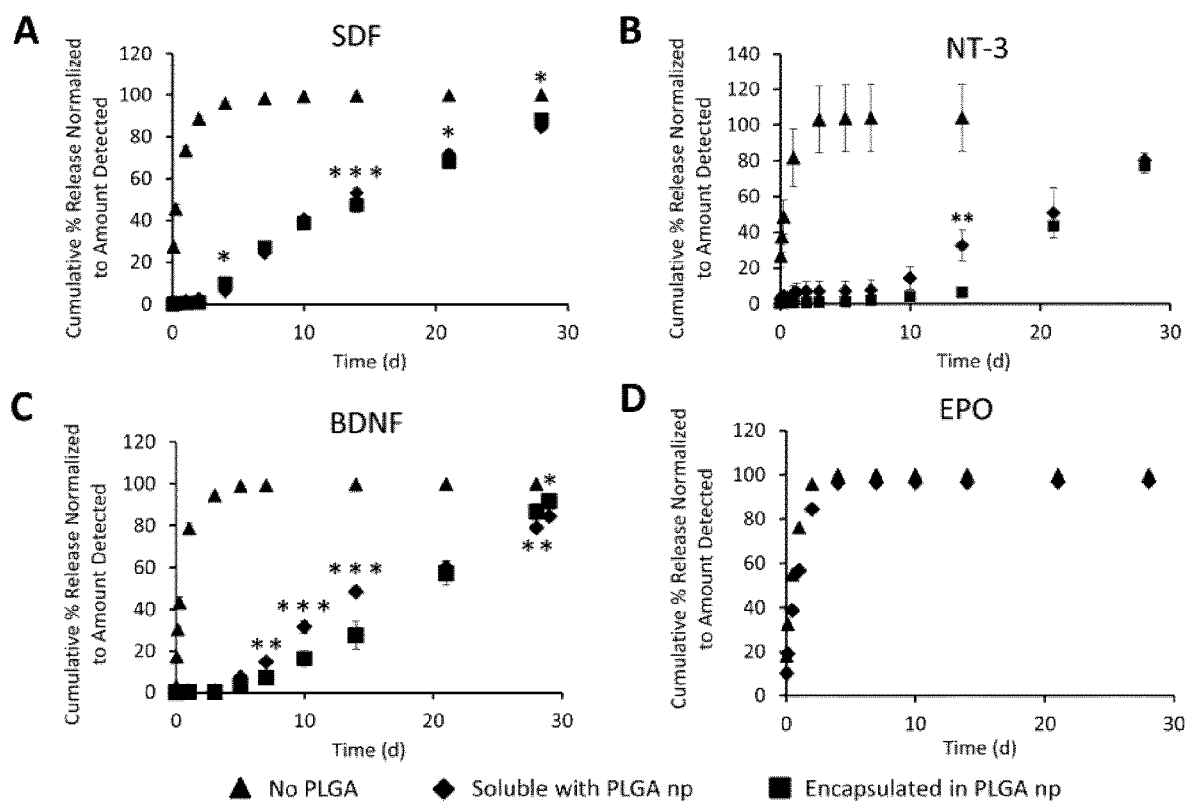
FIG. 2A shows that stromal cell-derived factor (SDF1α, pI 10.9, MW 8 kDa, 200 ng/release) has nearly identical release profiles whether encapsulated within PLGA nanoparticles, or simply mixed with blank PLGA nanoparticles in a hydrogel.
FIG. 2B shows that neurotrophin-3 (NT-3, pI 9.5, MW 27 kDa, 1000 ng/release) has nearly identical release profiles whether encapsulated within PLGA nanoparticles, or simply mixed with blank PLGA nanoparticles in a hydrogel.
FIG. 2C shows that brain-derived neurotrophic factor (BDNF, pI 10.9, 27 kDa, 300 ng/release) has nearly identical release profiles whether encapsulated within PLGA nanoparticles, or simply mixed with blank PLGA nanoparticles in a hydrogel.
FIG. 2D shows that Erythropoietin (EPO, pI ~4, MW 30 kDa, 84 ng/release) shows no attenuated release when mixed into a hydrogel composed of hyaluronan and methyl cellulose (HAMC) HAMC with PLGA nanoparticles vs. just HAMC alone (without PLGA nanoparticles), indicating that the phenomena observed with SDF, NT-3 and BDNF is based on short range electrostatic interactions between positively charged proteins and negatively charged PLGA (n=3, mean±standard deviation plotted).
Figure 3:
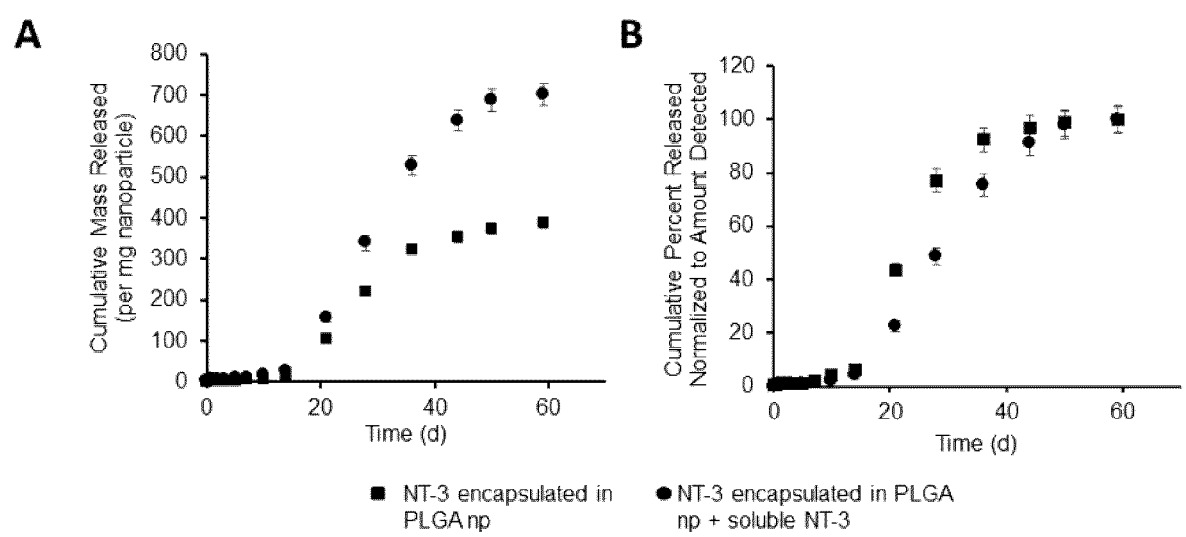
FIG. 3A shows the release of NT-3 from a PLGA nanoparticle/hydrogel drug delivery system (DDS) containing encapsulated NT-3 and soluble NT-3. This figure shows that the addition of soluble NT-3 increases the cumulative mass of NT-3 released from the PLGA nanoparticle/hydrogel DDS.
FIG. 3B shows the release of NT-3 from a PLGA nanoparticle/hydrogel DDS containing encapsulated NT-3 and soluble NT-3. This figure shows that the addition of soluble NT-3 does not increase the cumulative percent release. The release profile remains largely unchanged (n=3, mean±standard deviation plotted).

From the flatness of the plateaus in the cumulative percent released (FIG. 2, FIG. 3 (20)) it is contemplated that $|u_0| \gg k_B T$ and so chose the large value $u_0 = -10 k_B T$. This leaves the degradation rate, the near-unity carrying capacity, and the barrier height. These are determined by fitting the highest concentration (10 wt %) release curve, which has the most pronounced effects due to degradation. The parameters found are $K=(0.350\pm0.025)a^{-3}$, $\varepsilon_0=(1.025\pm0.025)\ k_B T$, and $r_0=(0.37\pm0.02)\ d^{-1}$. All other simulations were run using the same parameters with a combined reduced chi squared value $x_{red}^2=3.9$.

In Vivo BDNF Experiments

Endothelin-1 Stroke Injury

Stroke surgeries were performed as previously described [4]. Mediolateral (ML) and anteroposterior (AP) coordinates were measured relative to bregma and dorsoventral coordinates were measured relative to the skull surface. Male Long-Evans rats were anesthetized with isoflurane, shaved and positioned in a Kopf stereotaxic apparatus. An incision was made in the scalp and a retractor used to hold the skin in place. A 2.7 mm burr hole was drilled using a trephine drill bit (Cat. #18004-27, Fine Science Tools Inc., Vancouver, BC, Canada), centered at AP +1.15 mm and ML +2.5 mm. A durectomy was performed using a surgical microscope to aid the micro-dissection. The vasoconstricting peptide, Endothelin-1 (ET-1) (400 pmol/μL in ddH$_2$O, Cat. #05-23-3800, Calbiochem, Gibbstown, N.J., USA) was injected using an automated pump (Pump 11 Elite Nanomite, Harvard Apparatus, Saint-Laurent, QC, Canada) fitted with a 10 μL Hamilton syringe with a 26 G, 45° bevel needle (Model 1701 RN, Hamilton). Two injections were made in the primary motor cortex:

1. AP+2.3 mm, ML+2.5 mm, DV−2.3 mm
2. AP 0 mm, ML+2.5 mm, DV−2.3 mm.

The needle was lowered to −2.4 mm DV at each injection site and then raised DV+0.1 mm for the final DV−2.3 mm coordinate. Once in position, the needle was left for one minute to equilibrate. Following equilibration, ET-1 was injected at 0.5 μL/min until a volume of 1 μL had been injected. After a 1-minute pause, an additional 1 μL was injected at the same rate. Needles were allowed to equilibrate for 3 minutes following injection completion and then slowly withdrawn. A 2.3 mm diameter circle of medical grade silicone sheeting (Cat. #CUST-20001-005, BioPlexus, Ventura, Calif., USA) was placed on the tissue to prevent the tissue from sticking to anything above it and a small piece of Surgifoam® gelatin sponge (Cat. #1972, Ethicon, Markham, ON, Canada) was pre-soaked in saline until saturated and placed in the trephine hole on top of the silicone sheeting, filling the space to prevent swelling. Ortho-Jet™ BCA dental cement (Cat. #1334CLR, Lang Dental, Wheeling, Ill., USA) was used to cover and seal the hole and the scalp was sutured closed.

BDNF Diffusion into Stroke-Injured Rat Brain Tissue

PLGA nanoparticles were suspended in aCSF and BDNF in aCSF (0.1% BSA) was mixed into the HAMC composite at a concentration of 0.33 μg/μL. Four days post-stroke, rats were anesthetized with isoflurane, positioned in a stereotaxic apparatus and the previously made incision re-opened. Dental cement, gel foam and silicone sheeting was removed to expose the brain surface. A durectomy was performed using a surgical microscope to avoid damage to the pial vessel layer. A 5.9 mm diameter polycarbonate disk (spacer from brain infusion kit, Cat. #0008851, ALZET, Cupertino, Calif., USA) with a 2.7 mm diameter concentric hole was placed onto the skull surface with the hole aligned with the hole in the skull. The disk was fixed in place with bone glue (Loctite® 454™, Henkel Corporation, Rocky Hill, Conn., USA), and the BDNF-loaded HAMC composite was deposited on the surface of the brain tissue, filling the void formed by the skull and disk.

A second 5.9 mm diameter polycarbonate disk with no hole was glued on top of the first disk, the entire assemblage was encased in dental cement and the scalp was sutured closed. Identical procedures were performed on vehicle control animals, with aCSF (0.1% BSA) substituted for BDNF. Animals were sacrificed 13 and 20 days post-injury (n=3 per endpoint), brains were sectioned in 300 μm segments from the surface of the cortex, and ELISA was used to quantify BDNF in each segment of the tissue. Vehicle control brains were used to generate the ELISA standard curve.

Effect on Functional Recovery

Male Long-Evans rats were handled for one week and then trained in the Montoya staircase forelimb reaching task for two weeks, twice each day prior to ET-1 stroke surgeries. Stroke surgeries were performed as described previously, with the exception that the BDNF-loaded composite was delivered at the time of injury, immediately following the ET-1 injections and durectomy, negating the need for a second surgery. Functional recovery was assessed using the staircase reaching task at 1, 3, and 5 weeks post-injury.

Effect on Neural Tissue

At 7 weeks post-injury, all animals were sacrificed and brains were extracted and fixed in 4% paraformaldehyde for 10 days followed by cryoprotection in 15% and then 30% sucrose. Cryoprotected brains were snap-frozen with isopentane and sliced into 30 μm coronal sections using a cryostat. Sections stained for synaptophysin (Syn) and NeuN were first permeabilized for 15 minutes (1% Triton X-100 in PBS) at room temperature, blocked for 30 minutes (0.1% Triton X-100 and 5% BSA in PBS) and incubated with rabbit anti-synaptophysin (2 μg/mL in blocking solution, ab23754, Abcam, Cambridge, Mass., USA) primary antibody, mouse anti-NeuN (2 μg/mL in blocking solution, MAB377, Millipore Inc., Billerica, Mass., USA) primary antibody and Hoechst 33342 nuclei stain (1 μg/mL, Cat. #62249, Invitrogen Inc., Burlington, ON, Canada) at room temperature for 2 hours. Sections were then washed 3 times for 5 minutes in PBS and incubated in AlexaFluor 546 goat anti-rabbit IgG (0.001 mg/mL in blocking solution, A11035, Invitrogen Inc., Burlington, ON, Canada) and AlexaFluor 488 highly cross-adsorbed secondary antibody for 1 hour at room temperature. Sections were washed 3 times for 5 minutes in PBS, and mounted with ProLong® Gold Antifade Mountant (Cat. #P36934, Thermo Fisher Scientific, Mississauga, ON, Canada).

Coronal sections spaced 250-500 μm apart were chosen between AP +4.0 mm and AP −1.0 mm relative to bregma to assess infarct size and synaptic plasticity. Images were taken with a 20× objective on an Axio Scan.Z1 Slidescanner (Zeiss, Oberkochen, Germany), using consistent microscope settings for each section. Lesion area was defined as the area lacking regular NeuN$^+$ staining, using the contralesional hemisphere as a reference. ImageJ software was used to measure the lesion area for 10 sections per animal. These areas were first multiplied by the inter-section AP distance to determine the average volume of damage between sections and then added to determine total lesion volumes.

As a measure of synaptic plasticity, Syn+ pixels were quantified in 500 μm×500 μm cortical regions of interest in both ipsilesional and contralesional hemispheres. Regions of interest were adjacent to the lesion on either side of the cavity (R1), 500 μm away from the lesion on either side of the cavity (R2), inner cortex and outer cortex. 5 sections were analyzed per animal using the "Moments" thresholding algorithm in ImageJ software to convert Syn+ pixels to white and Syn− pixels to black. The number of white pixels in each region of interest was counted automatically using ImageJ and the average pixel densities for R1 and R2 regions were calculated by taking the average of the pixel density on either side of the cavity.

Statistical Analysis

Statistical analysis was performed using GraphPad Prism software. For all tests * p<0.05,  p<0.01, * p<0.001. Releases were analyzed using two-way analysis of variance (ANOVA) followed by the Sidak test for multiple comparisons if there were two groups or Tukey's test for multiple comparisons if there were more than two groups. Activity of NT-3, SDF1α, and BDNF were analyzed using one-way ANOVA followed by Dunnett's post hoc test comparing to the control. BDNF in vivo study behavioural results were analyzed using a repeated measures one-way ANOVA followed by Tukey's test for multiple comparisons. Lesion volume and synaptophysin immunohistochemistry results were analyzed using a one-way ANOVA followed by Tukey's test for multiple comparisons.

The following calculations have been used in the present disclosure.

1. Calculation of the Relative Surface Area for PLGA Nanoparticles of Different Sizes Assuming spherical nanoparticles, the mass of nanoparticles within the gel is given by:

$$m = \rho N \frac{4}{3}\pi r^3$$

where N is the total number of nanoparticles within the gel. Given equal masses of two different nanoparticle populations where $r_2=3r_1$ and assuming equal nanoparticle densities:

$$\rho N_1 \frac{4}{3}\pi r_1^3 = \rho N_2 \frac{4}{3}\pi (3r_1)^3$$

So, $$N_1 = 27 N_2$$

The total nanoparticle surface area within the gel is:

$$N 4\pi r^2$$

Therefore, $$S_1 = N_1 4\pi r_1^2$$

$$S_2 = \left(\frac{N_1}{27}\right) 4\pi (3r_1)^2$$

$$S_2 = \frac{9}{27} S_1 = \frac{S_1}{3}$$

So for a nanoparticle 3 times the radius, we obtain three times less surface area for the same mass.

2. Calculation for Maximum Surface Coverage

These calculations are done using SDF (MW~8000 Da) as an example. Assuming a spherical (globular) protein with hydrodynamic radius of approximately 2 nm and a nanoparticle radius of approximately 150 nm (based on our DLS measurements), we have:

$$A_{protein} = \pi(2)^2 = 12.57 \text{ nm}^2$$

$$SA_{particle} = 4\pi(150 \text{ nm})^2 = 2.83 \times 10^5 \text{ nm}^2$$

This means there would be approximately $$\frac{2.83 \times 10^5 \text{ nm}^2}{12.57 \text{ nm}^2} = 22513$$

proteins per nanoparticle given complete surface coverage. The mass of this number of proteins is:

$$m_{protein} = \frac{22513 \times MW}{N_A} = \frac{22513 \left(8000 \frac{g}{mol}\right)}{6.02 \times 10^{23}} = 2.99 \times 10^{-16} \text{ g}$$

The mass of a nanoparticle is:

$$m_{particle} = \frac{4}{3}\pi r^3 \rho = \frac{4}{3}\pi (0.000015 \text{ cm})^3 \left(1.5 \frac{g}{cm^3}\right) = 2.12 \times 10^{-14} \text{ g}$$

Assuming a density of 1.5 g/cm³. So the ratio of protein to polymer by mass that gives 100% coverage is:

$$\frac{2.99 \times 10^{-16} \text{ g}}{2.12 \times 10^{-14} \text{ g}} \times 100\% = 1.41\%$$

Results

Sustained Release without Encapsulation

The release of three proteins from two hydrogels with and without embedded PLGA nanoparticles were tested: SDF from a click-crosslinked methylcellulose hydrogel (XMC) [2] (FIG. 2A), and NT-3 (FIG. 2B) and BDNF (FIG. 2C) from a physical blend of hyaluronan and methyl cellulose (HAMC). The diffusional release of SDF, NT-3, and BDNF from the hydrogel alone is rapid (shown at 22 in FIG. 2), generally reaching completion by day 2. By encapsulating the proteins in PLGA nanoparticles before mixing them into the hydrogel (composite XMC, composite HAMC), sustained release was achieved for at least 28 days with no burst (shown at 24); however, a delay in the release of 4-7 days was observed (FIG. 2, FIG. 3, (26)). Encapsulation efficiencies in PLGA nanoparticles of 49±4%, 47±2%, and 47±7% were achieved for SDF, NT-3, and BDNF, respectively.

In an effort to overcome this delay, additional protein was mixed directly into the hydrogel with the protein-loaded PLGA nanoparticles. An initial burst release followed by a sustained release was anticipated, reflecting fast diffusion from the hydrogel and slower diffusion from the nanoparticles.

Instead, an identical release profile was observed, with only the total amount of released protein increased (FIG. 3). Surprisingly, a similar release profile was observed when all of the protein was simply mixed into the hydrogel with blank PLGA nanoparticles (FIG. 2A-C). FIG. 2 shows a release profile for an un-encapsulated proteins and nanoparticles, and the analogous release profile for proteins encapsulated in nanoparticles.

Figure 4:
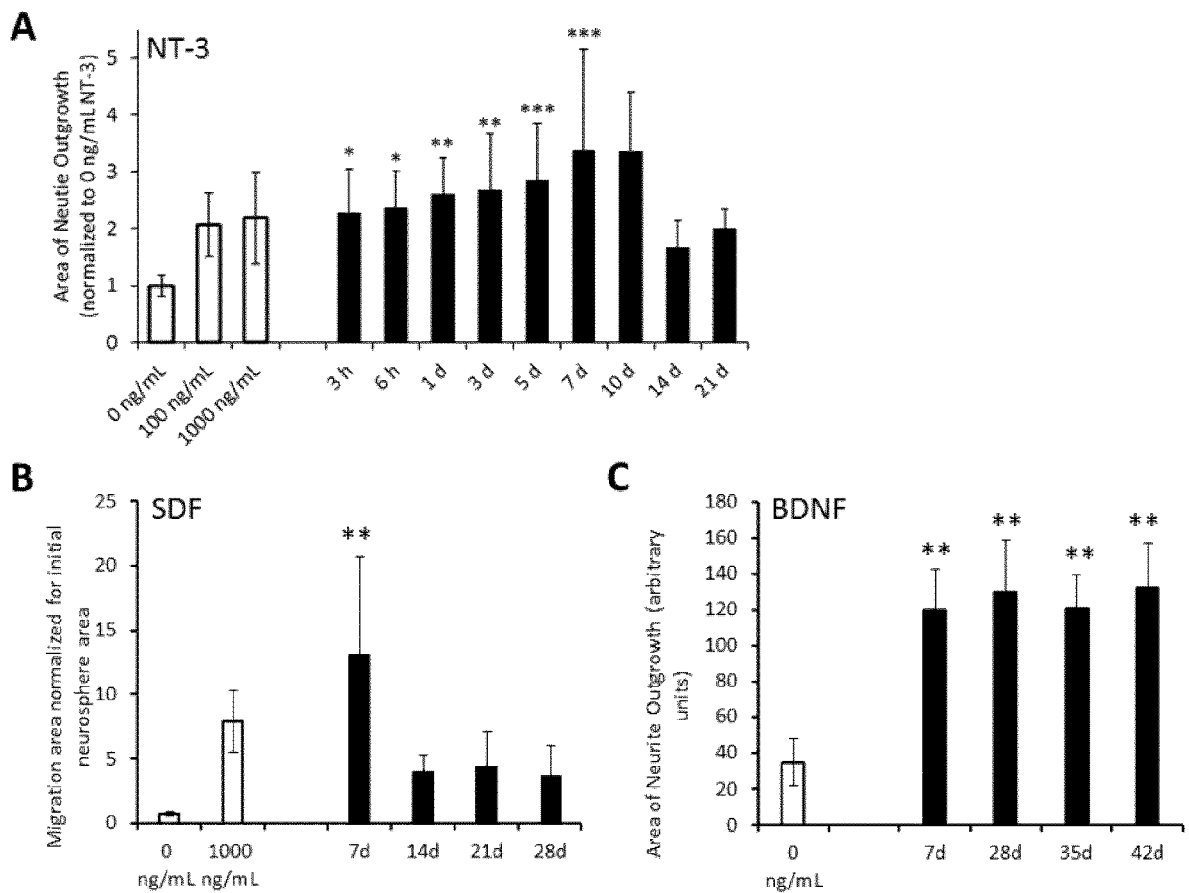
FIG. 4A shows the bioactivity of released NT-3. This was assessed using a dorsal root ganglion (DRG) neurite outgrowth assay. Released NT-3 elicits significantly increased neurite outgrowth for up to 10 days compared to a 0 ng/mL control, with a trend towards increased outgrowth for 21 days (n=3, mean±standard deviation plotted).
FIG. 4B shows the bioactivity of released SDF. This was assessed using a neurosphere migration assay. Released SDF caused significantly higher neural stem/progenitor cell migration for up to 7 days compared to a 0 ng/mL control, with a trend towards increased migration for 28 days (n=5 independent releases, mean±standard deviation plotted).
FIG. 4C shows the bioactivity of BDNF. This was assessed using a DRG neurite outgrowth assay. Released BDNF elicits significantly increased neurite outgrowth for 42 days compared to a 0 ng/mL control (n=3, mean±standard deviation plotted). (* p<0.05,  p<0.01, * p<0.001).

Importantly, all proteins remained bioactive when released using this encapsulation-free method (FIG. 4) with all of the protein incorporated into the system being available for release. This overcomes the <50% efficiency obtained with PLGA nanoparticle encapsulation.

Adsorption Governed by Electrostatic Interactions

Figure 5:
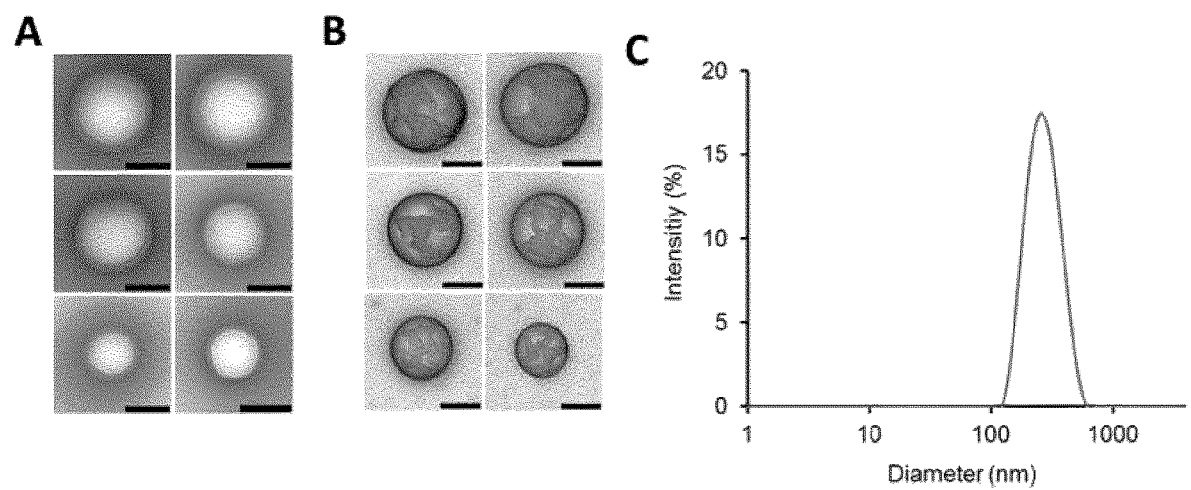
FIG. 5A shows representative transmission electron microscopy (TEM) images of PLGA nanoparticles used in this study stained with ammonium molybdate. Scale bar is 100 nm.
FIG. 5B shows representative TEM images of PLGA nanoparticles used in this study stained with uranyl acetate. Scale bar is 100 nm.
FIG. 5C shows a representative dynamic light scattering trace of the nanoparticles used in this study. Nanoparticles have an average diameter of ~300 nm with a PDI of ~0.2.
Figure 6:
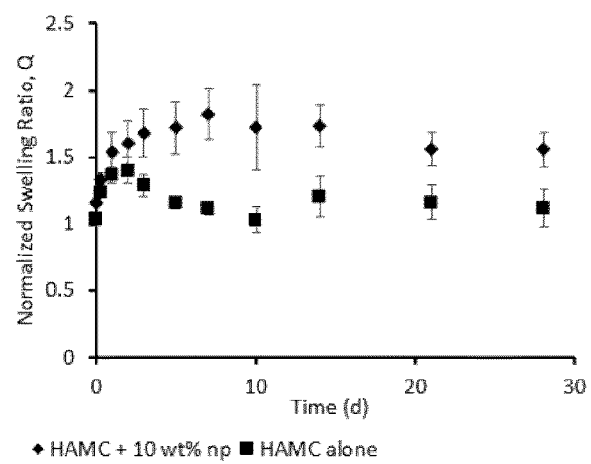
FIG. 6 shows the swelling of HAMC hydrogels with and without PLGA nanoparticles. HAMC with 10 wt % PLGA nanoparticles has a significantly higher swelling ratio than HAMC alone between 3 and 28 days (p<0.05, n=3, mean±standard deviation plotted).

To understand the release mechanism, the physical characteristics of this encapsulation-free release system were examined. Nanoparticle morphology and size were characterized by transmission electron microscopy (TEM) and dynamic light scattering (DLS). Nanoparticles were spherical with a relatively smooth surface and an average diameter of 293±19 nm with a PDI of 0.21±0.02 by DLS (FIG. 5). Zeta potential measurements showed that the surface of the PLGA nanoparticles was negatively charged (−14.0±0.7 mV), in agreement with previous reports [5], [6]. The swelling ratio of HAMC was compared to that of composite HAMC (i.e., PLGA nanoparticles dispersed in HAMC). Composite HAMC had a significantly higher swelling ratio after 3 days compared to HAMC alone (FIG. 6).

SDF, NT-3, and BDNF all have a net positive charge at physiological pH with isoelectric points (pI) of 10.9 for SDF, 9.5 for NT-3, and 10.1 for BDNF. It was postulated that the observed delayed release was primarily caused by adsorption due to short-range electrostatic interactions between the protein and the PLGA nanoparticles. To test this hypothesis, the release of erythropoietin (EPO), another protein which has shown benefit in CNS repair strategies and has a pI of 3.3-4.3, making it negatively charged at physiological pH, was examined. Soluble EPO was released just as rapidly from composite HAMC as from HAMC alone, with complete release observed after 2 days (FIG. 2D). This is consistent with the hypothesis that adsorption is mediated by electrostatic interactions.

Figure 7:
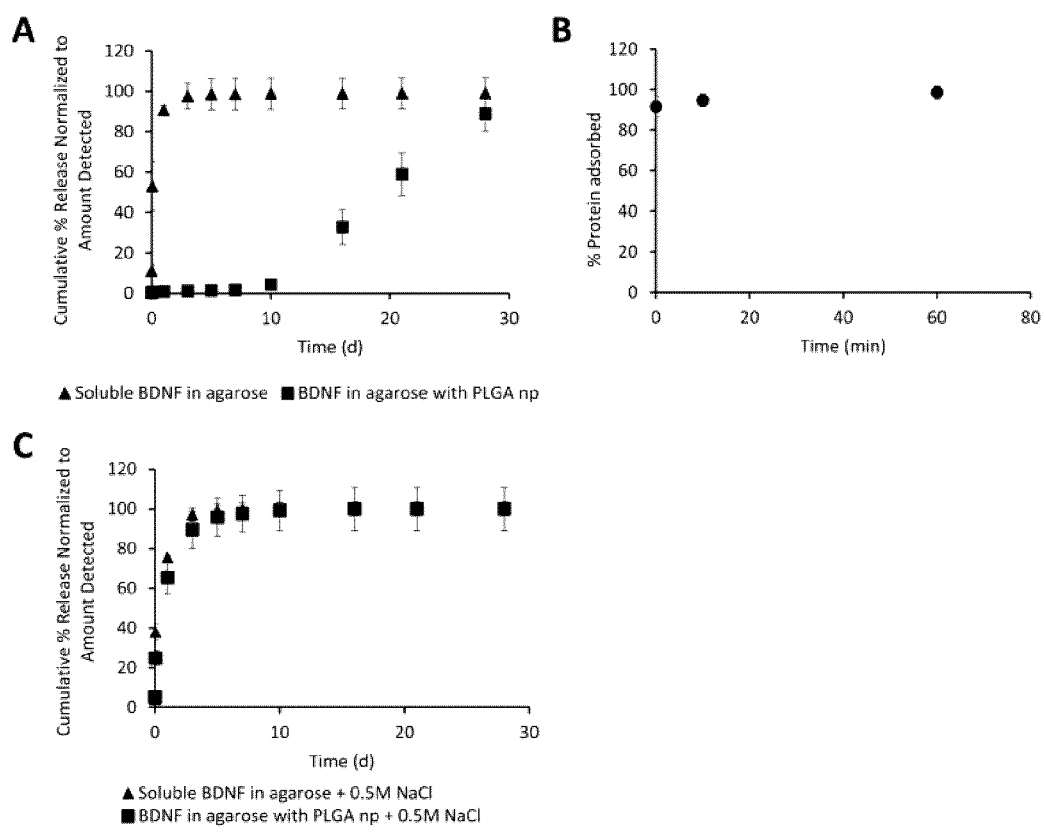
FIG. 7A shows that BDNF shows the same delayed and sustained release profile from agarose containing PLGA nanoparticles as from HAMC with PLGA nanoparticles while diffusional release from agarose alone is still fast.
FIG. 7B shows that almost all soluble BDNF is adsorbed to PLGA nanoparticles after incubation, even at short times.
FIG. 7C shows that 0.5 M NaCl completely disrupts the interaction of BDNF with the PLGA nanoparticles resulting in purely diffusional release (p>0.05 for all timepoints, n=3 for all releases, mean±standard deviation plotted).

The hydrogel itself seems to have a minimal role in controlling release, as the release of SDF from XMC and that of NT-3 and BDNF from HAMC show similar profiles. To examine this further, both XMC and HAMC were replaced with another common gel, agarose. Release of soluble BDNF from agarose alone was the same as that from HAMC alone, while release of soluble BDNF from agarose containing PLGA nanoparticles exhibited the same delayed release profile that was observed with HAMC containing PLGA nanoparticles (FIG. 7A). Incubation of BDNF with free PLGA nanoparticles in aCSF at the same ratio of protein to PLGA as in the hydrogels, resulted in almost complete adsorption within minutes (FIG. 7B), suggesting that the mechanism for controlled release is mediated by the nanoparticles, not the hydrogel.

Adsorption mediated by electrostatic interactions can be disrupted by raising the level of competing ions in solution. When the salt concentration of the release media was raised from 149 mM (physiologically relevant) to 0.5 M, release of BDNF from the agarose PLGA nanoparticle composite was fast, and almost identical to the release profile observed in the absence of the nanoparticles (FIG. 7C).

Tuning Release by Controlling the Surface Area of PLGA Nanoparticles

Figure 8:
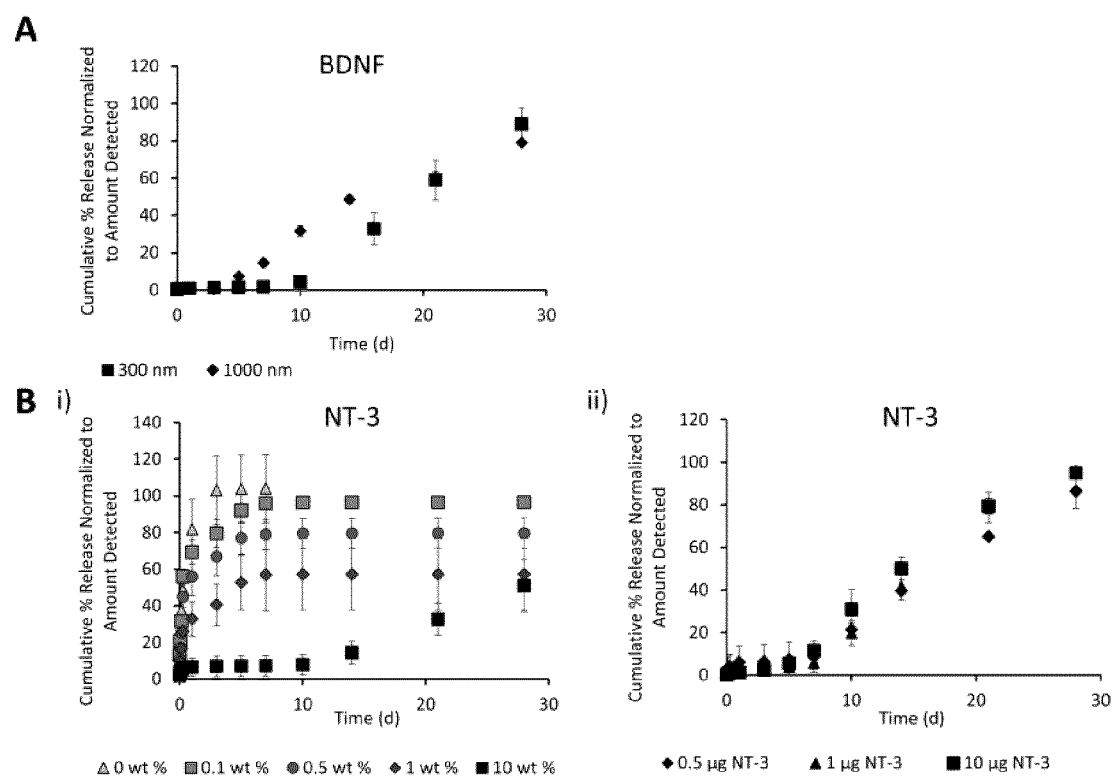
FIG. 8A shows that release of BDNF from composite HAMC begins earlier with 1000 nm diameter PLGA nanoparticles than 300 nm diameter PLGA nanoparticles while keeping PLGA nanoparticle mass constant.
FIG. 8B(i) shows the release of NT-3 from composite HAMC with 0, 0.1, 0.5, 1, and 10 wt % PLGA nanoparticles. Cumulative percent of NT-3 released is significantly lower for 10 wt % PLGA nanoparticles than all other curves at t>1d (p<0.05). Cumulative percent of NT-3 released is significantly higher with 0 wt % PLGA nanoparticles than 0.1 wt % (t=1d, p<0.05), 0.5 wt % (1d≤t≤3d, p<0.05), 1 wt % (t>3 h, p<0.05).

To further investigate the role of PLGA nanoparticles in controlling release, we examined the role of PLGA nanoparticles surface area, since the amount of protein adsorbed is proportional to the available surface area. The release of BDNF from composite HAMC containing either 300 nm or 1000 nm-diameter nanoparticles was investigated. Assuming similar densities and spherical nanoparticles, the 1000 nm nanoparticles would have 3 times less available surface area than the 300 nm nanoparticles for the same mass (see calculations in Methods section above). Consistent with the hypothesis that the interaction between PLGA nanoparticles and positively charged proteins controls release, the larger nanoparticles (with the overall lower surface area) resulted in faster release (FIG. 8A).

The available PLGA nanoparticle surface area can similarly be controlled by the concentration of nanoparticles within the gel. A direct correlation was observed between the number of PLGA nanoparticles dispersed in the hydrogel and the release rate of NT-3 from composite HAMC. With the lowest concentration of nanoparticles (FIG. 8B, i, 0.1 wt %), there was a faster initial release rate that approached the diffusion-controlled release profile of NT-3 from HAMC alone (FIG. 8B, i, 0 wt %). As the concentration of nanoparticles increased, the release rate slowed. Interestingly, the concentration of NT-3 could be increased by 20-fold (from 0.5 μg to 10 μg) in the 10 wt % PLGA nanoparticles composite while maintaining a virtually identical release profile (FIG. 8B, ii). Thus, a facile method to control both release rate and amount of protein released was demonstrated.

Tuning Release by Modifying Adsorption Affinity

Figure 9:
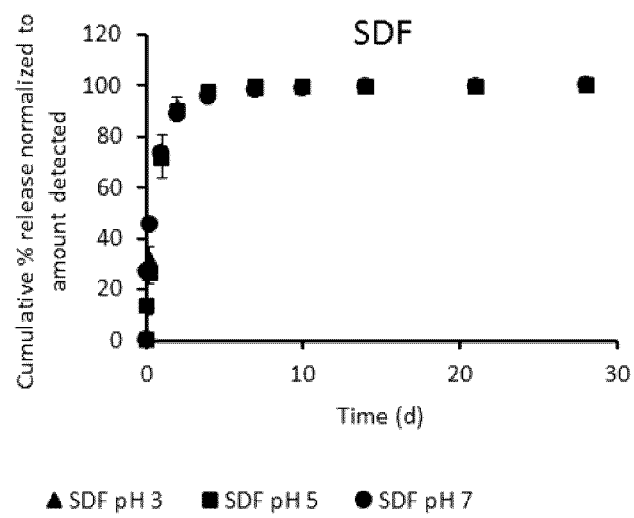
FIG. 9 shows the release of soluble SDF from a crosslinked methylcellulose hydrogel (XMC) alone into artificial cerebrospinal fluid (aCSF) at pH 3, 5, or 7. Release results indicate no effect of varying pH on protein detection by enzyme-linked immunosorbent assay (ELISA) (n=3, mean±standard deviation plotted).
Figure 10:
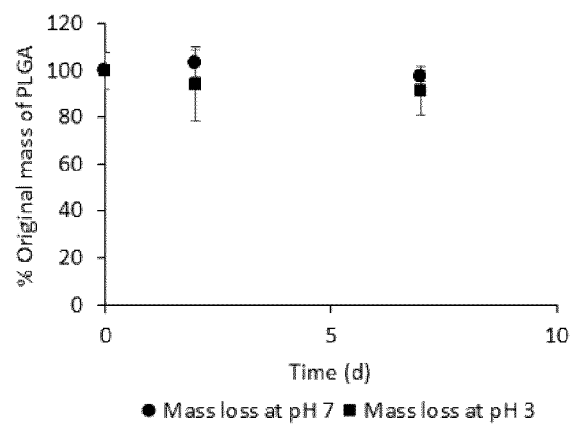
FIG. 10 shows the mass loss of PLGA from the release system at pH 3 and pH 7. There is no significant mass loss of PLGA from the hydrogel over the first 7 days of release, regardless of pH (p>0.05 at all timepoints, n=3, mean±standard deviation plotted).

Since adsorption can be controlled by modifying the interaction strength between the proteins and PLGA nanoparticles, the role of supernatant pH on protein release from our DDS was examined, as supernatant pH would affect both the charge of the protein and that of the PLGA nanoparticle surface. SDF was released from composite XMC into media at pH 3, 5, and 7. The release rate of SDF from composite XMC (i.e., in the presence of nanoparticles) significantly increased with decreasing pH (FIG. 11A); yet, in the absence of nanoparticles, the release rate of SDF was unaffected by decreasing pH (FIG. 9). Moreover, since there was no significant mass loss of PLGA from the hydrogel over the first 7 days of release at either pH 3 or pH 7, yet the release profiles are drastically different (FIG. 10), the difference in release cannot be explained by destabilization of the gel at lower pH. Thus, these data indicate that pH can be used to control release and that at lower pH, the carboxylate anions of PLGA are protonated, the electrostatic interaction between PLGA anions and protein cations is diminished.

Figure 11:
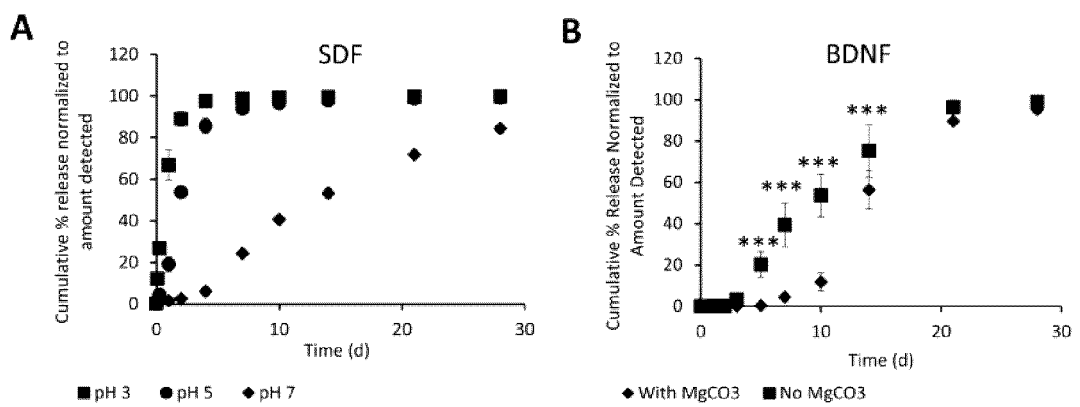
FIG. 11A shows the release of SDF from composite XMC into media at pH 3, 5, or 7. Cumulative percent release of SDF is significantly greater at pH 3 than pH 5 (t<10 d, p<0.01) and pH 7 (t>0 d, p<0.0001) likely because PLGA carboxylate anions are protonated to carboxylic acids, thereby reducing electrostatic interactions with positively charged proteins.
FIG. 11B shows the release of BDNF from HAMC with PLGA nanoparticles with or without encapsulated magnesium carbonate ($MgCO_3$). Release is delayed with encapsulated $MgCO_3$, a basic salt, which neutralizes acidic degradation products and thereby maintains a higher/neutral local pH (n=3 for all releases, mean±standard deviation plotted).

To investigate the effect of local pH on protein release, the release of BDNF from composite HAMC containing PLGA nanoparticles was compared with and without encapsulated $MgCO_3$. As PLGA is known to degrade to acidic products by bulk degradation, the encapsulation of basic salts has been used to delay pH changes within PLGA nanoparticles [7]. Release of soluble BDNF from composite HAMC had a delay of approximately 7-10 days with encapsulated $MgCO_3$ (FIG. 11B). In contrast, in the absence of $MgCO_3$, the delay was shortened to just 4 days. This suggests that the mechanism for protein release is related to a change in PLGA charge from negative carboxylate anions to neutral carboxylic acids, which is slowed in the presence of $MgCO_3$.

Monte Carlo Simulations

Figure 12:
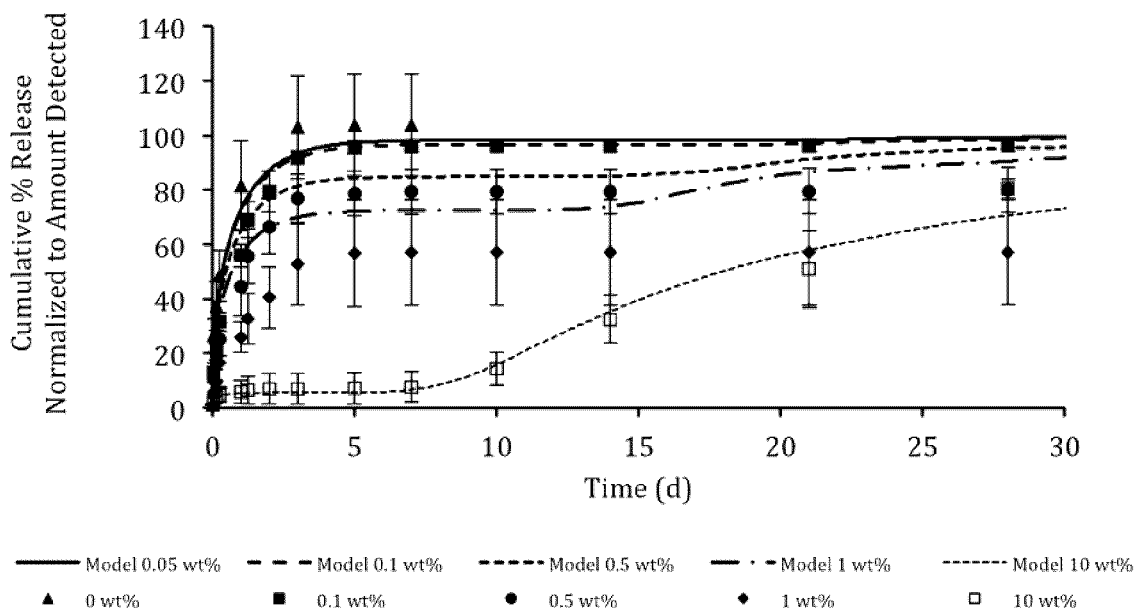
FIG. 12 shows the Monte Carlo simulations agree well with experimental results. Release of NT-3 from HAMC with 10 wt % PLGA nanoparticles (FIG. 8B,i) was fit using 3D on-lattice Monte Carlo simulations. Simulations were then run for all other nanoparticle concentrations in FIG. 8B,i using the same parameters. Symbols represent data while solid lines represent the simulation results. The combined reduced chi squared value for all simulations was $x_{red}^2=3.9$.

As a further test of the hypothesis for release mechanism, on-lattice Monte Carlo simulations were performed of protein release from a hydrogel with a stochastic logistic-population model for the degradation of the PLGA nanoparticles. The nanoparticles were modeled as cubic obstacles possessing short-range interactions with the proteins. Both a deep attractive potential well to model electrostatic adsorption and a low repulsive barrier to adsorption were included, with both potentials approaching zero as the nanoparticles degrade. This scheme is observable qualitatively in heuristic two dimensional simulations. This model was used to reproduce the release curves obtained in FIG. 8B,i by fitting the simulation parameters to best match the 10 wt % PLGA nanoparticles case, then using the same parameters for all other simulations without any additional fitting (FIG. 12). The combined reduced chi squared value for all simulations was $x_{red}^2=3.9$.

While the simulation parameters were chosen to best reproduce the 10 wt % curve with its clear plateau region and secondary rise, the 0 wt %, 0.1 wt %, and 0.5 wt % curves are also well described. Intermediate concentrations such as 1 wt % show the least agreement, demonstrating the implicit effects of finite gel size on the relative significance of protein-nanoparticle interactions and diffusion in Monte Carlo simulations.

Un-Encapsulated BDNF Delivery In Vivo

Although sustained released of un-encapsulated BDNF was observed in vitro, in vivo efficacy of the delivery system is the ultimate goal. Un-encapsulated BDNF was delivered to ET-1 stroke-injured rats 4 days post-injury and protein concentration was quantified at two time-points to determine an in vivo diffusion profile. BDNF was detectable above endogenous levels at both 13 and 20 days post-delivery, as measured by tissue ELISA. At the 13-day timepoint, a peak in the detected BDNF was observed at 900 μm from the surface of the cortex, quickly dropping off in the next segments of tissue. At 20 days, the BDNF had diffused deeper, with less of the detected protein near the surface and a broader distribution, reaching deeper segments of the tissue. These diffusion profiles demonstrate the ability of this system to deliver therapeutic proteins to the stroke-injured brain in a sustained manner without the need for nanoparticle encapsulation.

Functional Recovery with Non-Encapsulated BDNF Delivery

To assess the effect of this therapeutic strategy on functional recovery following stroke, the BDNF-loaded composite was administered to stroke-injured rats that were trained to perform the Montoya staircase reaching assay. The composite was delivered immediately following ET-1 injections to minimize the number of surgeries, as well as to maximize potential for the neuroprotective effects of BDNF and the HAMC hydrogel. Groups were as follows: Sham (scalp incision and polycarbonate cap placement only), Injury (ET-1 stroke injury and cap placement), Vehicle (ET-1 stroke injury, cap placement and aCSF mixed with the PLGA-HAMC composite), and BDNF (ET-1 stroke injury, cap placement and un-encapsulated BDNF mixed with the PLGA-HAMC composite).

Week 1 staircase testing was used to assess the degree of injury and animals that were too injured (<20% baseline performance) or did not have a large enough injury (>60% baseline performance) were excluded in further analyses. Statistical testing by repeated measure ANOVA confirmed that the population of remaining animals exhibited a significant deficit compared to baseline performance.

At weeks 3 and 5 post-stroke, only animals that received the BDNF-loaded PLGA-HAMC composite demonstrated significantly improved performance in the staircase task relative to their injured performance at week 1. Injury and Vehicle groups did not exhibit significant improvements in performance relative to their week 1 scores at any of the timepoints tested. Thus, this therapeutic strategy provides some benefit for forelimb functional recovery following ischemic stroke injury.

Effect of Un-Encapsulated BDNF on Stroke-Injured Tissue

Lesion volume and synaptophysin expression were used to elucidate the mechanism behind the observed functional recovery in the BDNF-treated group. At week 7, animals were sacrificed and neural tissue was harvested to investigate any observable effects of the un-encapsualted BDNF treatment. For consistency, the same subset of animals that was used in behavioural analysis was used to determine tissue effects. Quantification of lesion volume with Hoechst and NeuN immunohistochemistry revealed a significant reduction in cortical lesion volume for animals treated with un-encapsulated BDNF when compared to the injury-only group.

Animals that received the HAMC-PLGA vehicle without BDNF also exhibited a trend toward decreased lesion volume. This was not significantly different from injury-only animals, but was also not significantly different from the lesion volume in the BDNF-treated group. A decrease in lesion volume was expected in the vehicle group due to the anti-inflammatory and wound healing effects of HA and previous studies that demonstrated this effect when delivered at the time of injury [8]. The addition of BDNF resulted in a greater reduction of lesion volume, likely through activation of the phosphoinositol-3 kinase (PI3K)/protein kinase B (AKT) pathway, which promotes survival of neurons and other cell types [9].

Synaptophysin expression, observed as $Syn^+$ pixels, was quantified for cortical regions of interest in both ipsilesional and contralesional hemispheres and compared between groups with regular one-way ANOVA. Significant increases in synaptophysin expression were observed in contralesional regions of interest R1 and R2 for BDNF-treated animals when compared against the corresponding regions in vehicle and injury groups. In ipsilesional sections, synaptophysin expression was markedly decreased in the R1 region, adjacent to the lesion, in injury animals when compared to vehicle animals. Increased synaptophysin expression in the contralesional hemisphere indicates that a certain degree of reorganization and compensatory action contributed to the enhanced functional recovery observed in the behavioural task. BDNF is widely known as an agent of plasticity, acting through the phospholipase C-γ (PLC-γ) pathway [9]. As this tissue effect was seen only in BDNF-treated animals, the addition of exogenous BDNF via this delivery strategy promoted synaptogenesis, enabling rearrangement of existing circuits to restore some of the lost function.

Discussion

Models of drug release from PLGA nanoparticles usually consider polymer degradation, erosion, and diffusion of the drugs through the resulting water-filled pores as rate determining. The results, however, show very similar release profiles for three different proteins whether they are encapsulated in PLGA nanoparticles or simply mixed with them, indicating that another mechanism must be involved.

Figure 13:
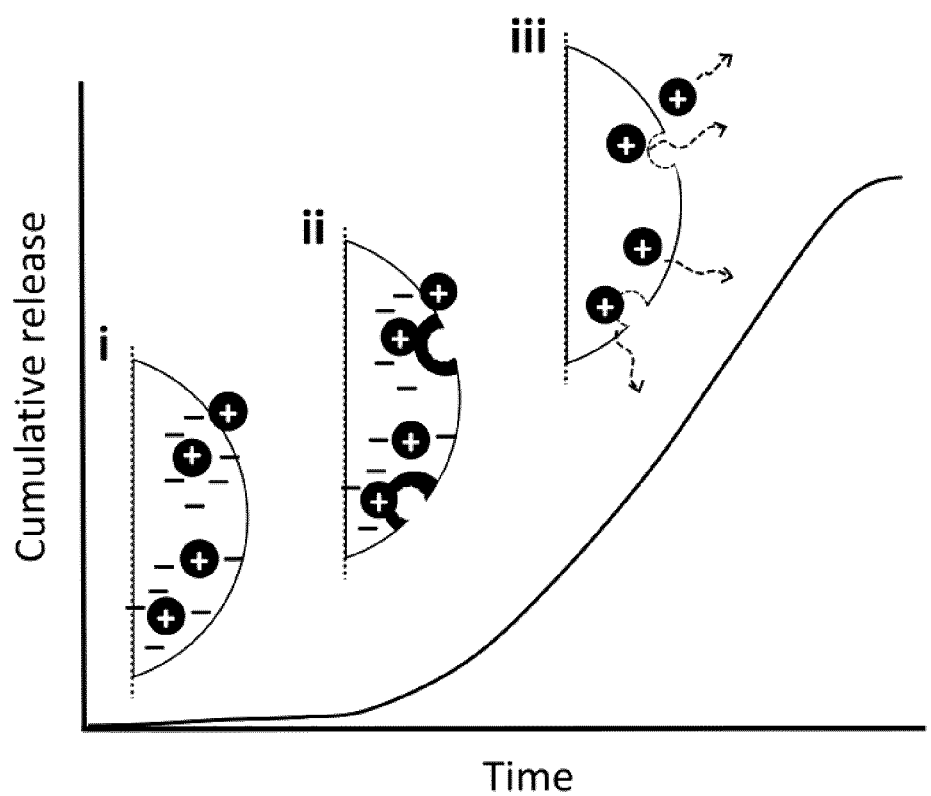
FIG. 13 shows that adsorption may be rate limiting for release of positively charged proteins from PLGA nanoparticles. (i) Initially, the protein is fully adsorbed to the negatively charged nanoparticle surface. (ii) As the nanoparticle begins to degrade, acidic components build up and decrease the local pH. (iii) At a certain threshold, the nanoparticle surface becomes neutral, weakening the electrostatic interactions with the positively charged proteins and initiating release.

Without be bound by any theory, it is postulated that initially the protein is fully adsorbed to the negatively charged nanoparticle surface (FIG. 13E, i). As the nanoparticle begins to degrade, acidic components build up and decrease the local pH (FIG. 13E, ii). At a certain threshold, the original negative carboxylate anion on the nanoparticle surface becomes protonated to carboxylic acid, thereby weakening the electrostatic interactions with the positively charged proteins and initiating release (FIG. 13E, iii).

Release can then be governed by nanoparticle degradation and protein diffusion and/or adsorption/desorption depending on the system.

It is possible that the presence of the PLGA nanoparticles affects the release of proteins simply by changing the gel mechanics. Methylcellulose forms a gel via hydrophobic interactions and its shear modulus increases upon incorporation of PLGA nanoparticles, suggesting additional hydrophobic interactions between MC and PLGA nanoparticles. These hydrophobic interactions have been postulated to affect the release rate of protein from PLGA nanoparticles. The results, however, show that the addition of PLGA nanoparticles actually increases the hydrogel swelling ratio likely due to the presence of carboxylate anions on the PLGA nanoparticle surface. Increased swelling of poly(acrylic acid) gels with the addition of polystyrene nanoparticles has been attributed to the sulfonic acid groups on the nanoparticle surface, and carboxylate anions have previously been found to affect the swelling of hydrogels.

Increased swelling should lead to an increased mesh size and subsequently increased release rate of a protein; however, the data shows the opposite effect, indicating an interaction between PLGA nanoparticles and protein. Additionally, changes in mesh size would be expected to affect all proteins, depending on their size; however, EPO, which has a larger molar mass than SDF and a similar molar mass to NT-3 and BDNF, does not show sustained release in the presence of PLGA nanoparticles. Thus gel mechanics are unlikely the mechanism controlling release of proteins from composite PLGA nanoparticle hydrogels.

Adsorption is recognized as one of the factors affecting the release of biomolecules encapsulated in PLGA particles and is a major cause of incomplete release. Adsorption of proteins at the surface of PLGA particles is also often cited as the cause of the initial burst observed in release from PLGA nanoparticle formulations and is attributed to a combination of electrostatic and hydrophobic interactions. Interestingly, the release of proteins adsorbed to the surface of PLGA particles is often fast (within the first 1-8 hours of release) and has not been fully studied.

In order to examine the possibility of a hydrogel effect, the release from agarose, an uncharged polymer with a different mechanism of gelation than either XMC or HAMC, was tested. The release profiles of BDNF were the same whether from composite HAMC or composite agarose, suggesting a specific interaction between the protein and the PLGA nanoparticles, not the hydrogel. When BDNF was incubated with PLGA nanoparticles alone at the same ratio used in the release studies, almost all the BDNF was removed from the supernatant within minutes, demonstrating a strong interaction with the PLGA nanoparticles.

Adsorption is governed by non-covalent interactions including electrostatic, hydrophobic and van der Waals forces. Given that SDF, NT-3, and BDNF are all positively charged at neutral pH, and a negatively charged protein (EPO) did not show the same release behaviour, it was hypothesized that electrostatic interactions were governing protein adsorption. The range of electrostatic interactions is governed by the Debye length. For this release system, the Debye length is very small (<1 nm), so long-range electrostatic interactions are not important; however, short-range interactions likely still exist. Electrostatic interactions such as these can be disrupted with an excess of ions. In fact, BDNF is often purified using ion exchange chromatography and a salt concentration of 0.5 M is within the range used for elution. When the release of BDNF from composite agarose was examined in the presence of 0.5 M NaCl, the release rate approached diffusional values.

Control over the release rate is essential for the success of sustained delivery formulations. Different parameters of the DDS and their effects on the release rate of soluble proteins were explored. Models of drug release controlled by adsorption/desorption demonstrate that release is governed by the number of available binding sites and the strength of the interaction.

Nanoparticle size can be readily varied by modifying the formulation conditions, and is therefore a facile method to control release. Assuming a similar density, smaller nanoparticles provide an overall larger surface area and would therefore increase the extent of adsorption. It was shown that BDNF released from HAMC with 300 nm nanoparticles showed a longer delay and slower release than that from HAMC with 1000 nm nanoparticles.

Since the protein loading and nanoparticle concentration are decoupled in our DDS, changing the nanoparticle concentration provides a simple method to tune release. In general, release of NT-3 is faster with lower nanoparticle concentrations. When the nanoparticle concentration is decreased from 10 wt % to 1 wt % with a constant amount of protein, a significant burst release is seen. On the other hand, increasing the protein concentration ten-fold while maintaining the nanoparticle concentration at 10 wt %, does not change the release profile of NT-3 despite an identical nanoparticle to protein mass ratio as the 1 wt % case above. A similar effect is seen in affinity-controlled release systems: as long as the available binding sites are in excess, release rate depends on the concentration of binding ligand (here the PLGA nanoparticles), not on the binding ligand to protein ratio.

Theoretically, complete surface coverage of the PLGA nanoparticles occurs at 1.41 wt % protein loading as calculated in the Method section. When increasing protein concentration, 0.1 wt % protein loading by mass was never exceeded due to the significant costs of these proteins; however, based on the calculations above, it is expected that a 1 wt % loading could be achieved without significantly altering the release profile. This suggests that the DDS could deliver substantially higher loadings than previously reported for PLGA encapsulation of therapeutic proteins such as NT-3, BDNF or nerve growth factor (NGF).

PLGA nanoparticles lose their negative charge at and below pH 5, thus decreasing their charge attraction to positively charged proteins. Increased release rates of SDF at pH 3 and 5 were observed compared to pH 7. Importantly, this is not due to gel destabilization at low pH, as there is no significant mass loss of PLGA nanoparticles over 7 days at pH 3 or pH 7. The ability to increase the release rate at acidic pH may have interesting implications for in vivo delivery at acidic sites, such as the tumor microenvironment.

In all of the release profiles, a constant, slow release phase was observed after the initial delay or burst. PLGA degrades by bulk degradation into acidic components that are often trapped within the nanoparticles prior to their dissolution, decreasing the pH inside the nanoparticle. It is postulated that this reduction in local pH reduces the magnitude of the protein-polymer interaction (as shown in the pH study) and initiates protein release as a certain pH threshold is reached. Thus, by controlling the pH change within the PLGA nanoparticles, it should be possible to eliminate or extend this delay. Indeed, encapsulation of a basic salt, $MgCO_3$, slowed the release of BDNF from PLGA nanoparticles dispersed in HAMC, likely by decreasing the rate of PLGA degradation and pH change within the nanoparticles. Similarly, PLGA polymers with different properties (molecular weight, end group, lactide to glycolide ratio) could also be used to formulate nanoparticles with various degradation rates to achieve different release profiles.

Agreement between the minimal Monte Carlo simulations and the experimental data further suggests that the release curves result from: 1) an initial diffusive regime during which proteins either escape the hydrogel or adsorb to a nanoparticle, 2) a plateau region, and finally 3) a secondary rise due to the release of the proteins following PLGA nanoparticles degradation. The model over predicts the initial burst for lower nanoparticle concentrations, especially the 1 wt % case, which is likely a result of the small finite size of the simulated system. The model also predicts an eventual rise (phase 3) for lower nanoparticle concentrations that was expected, but was not observed experimentally. It is possible that the releases were simply not taken to long enough time-points to observe this phase, or perhaps a portion of the protein is adsorbing irreversibly at longer timepoints when the pH changes are not as rapid. However, reproducing the general shape of the release curves and obtaining adequate agreement for five different release curves using a single set of parameters shows that the release hypothesis is robust.

Although the possibility that the polymer degradation, irrespective of the pH change, decreases the affinity of the protein for the nanoparticles cannot be ruled out, previous studies have shown that the available surface area for adsorption actually increases as the nanoparticle degrades, which would likely result in increased adsorption and slower release. Therefore it seems more likely that polymer degradation indirectly affects protein release through change in pH.

The in vivo results presented herein demonstrate that this DDS is able to sustain the release of un-encapsulated positively charged protein in vivo in addition to what was shown in vitro. Importantly, the delivered BDNF exhibits beneficial effects on tissue and functional recovery, indicating that bioactivity is preserved and that therapeutic concentrations are present in the tissue.

Using PLGA for release of bioactive proteins without encapsulation is a paradigm shift in controlled delivery, and the use of the well-established PLGA facilitates clinical translation. Furthermore, controlled release is obtained without any modifications to the protein that may affect activity. Tunable release is achieved by varying simple formulation parameters, and stimuli-responsive release is demonstrated by modifying environmental pH. The next step is the extension of these concepts to additional proteins. Although similar release profiles for three different proteins were shown, not all proteins can be expected to interact in the same way. A simple adsorption experiment could quickly ascertain whether this method is suitable for a given protein. The polymer composition (e.g. end group, lactide to glycolide ratio) might also be tailored to suit a particular protein. While not explored herein, in order to control the release of negatively charged proteins, PLGA nanoparticles could be coated with positively charged polymers such as chitosan or positively charged polymeric nanoparticles that degrade into basic components could be used instead. The results presented here provide the basis for a fundamental change in the way we use PLGA for protein delivery.

The combination of the zero initial burst release and multi-week release of bioactive molecules is very advantageous for many applications. Many drug-loaded polymer particles exhibit high burst release, namely rapid release of the loaded drug within the first 1 to 3 days, before the onset of polymer degradation. This is undesirable, as it reduces the amount of drug available for sustained release and could result in drug concentrations above the therapeutic threshold. For the release of proteins from PLGA particles, the burst release can be as high as >50% of the total amount released, while a burst release of <10% of the total amount released is rarely achieved.

However, by taking advantage of electrostatic interactions to control protein release from a nanoparticle/hydrogel composite system as disclosed herein, a burst release of <10% is attained. As a result, for this system a period of delayed release is observed, where the onset of linear release begins 2-5 days after delivery. This timing corresponds to the timing of the change in pH in the particle microenvironment due to polymer degradation.

Figure 14:
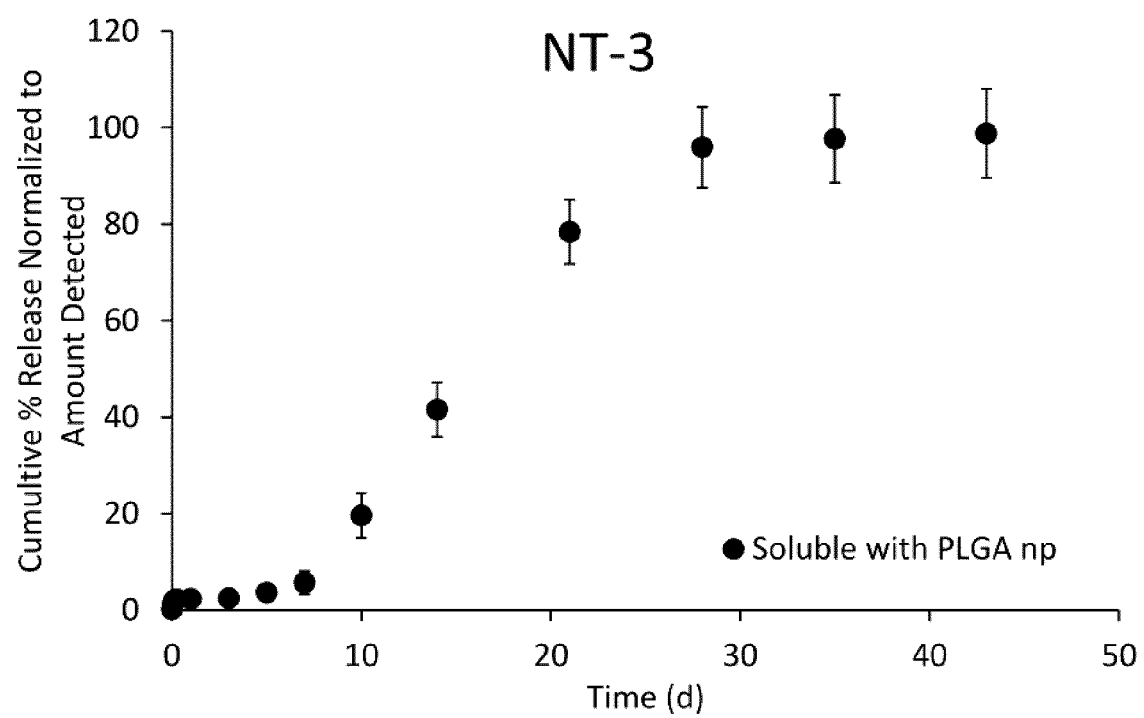
FIG. 14 shows a plot of cumulative % release normalized to amount detected versus time for NT-3 dispersed in the nanoparticle/hydrogel drug delivery system showing the NT-3 is released for up to 43 days.
Figure 15:
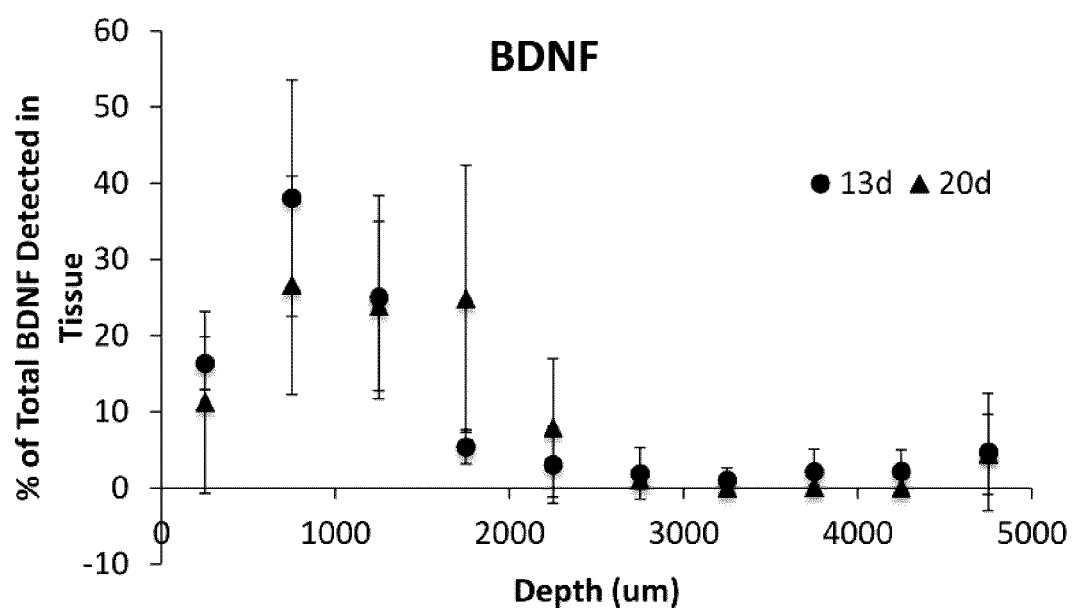
FIG. 15 shows a plot of % of total BDNF detected in stroke-injured rat brain tissue as a function of depth from the surface of the brain, demonstrating that BDNF is released from the composite, diffuses into the tissue and is detectable above endogenous BDNF levels at both 13 and 20 days post-delivery (n=3, mean±standard deviation plotted).
Figure 16:
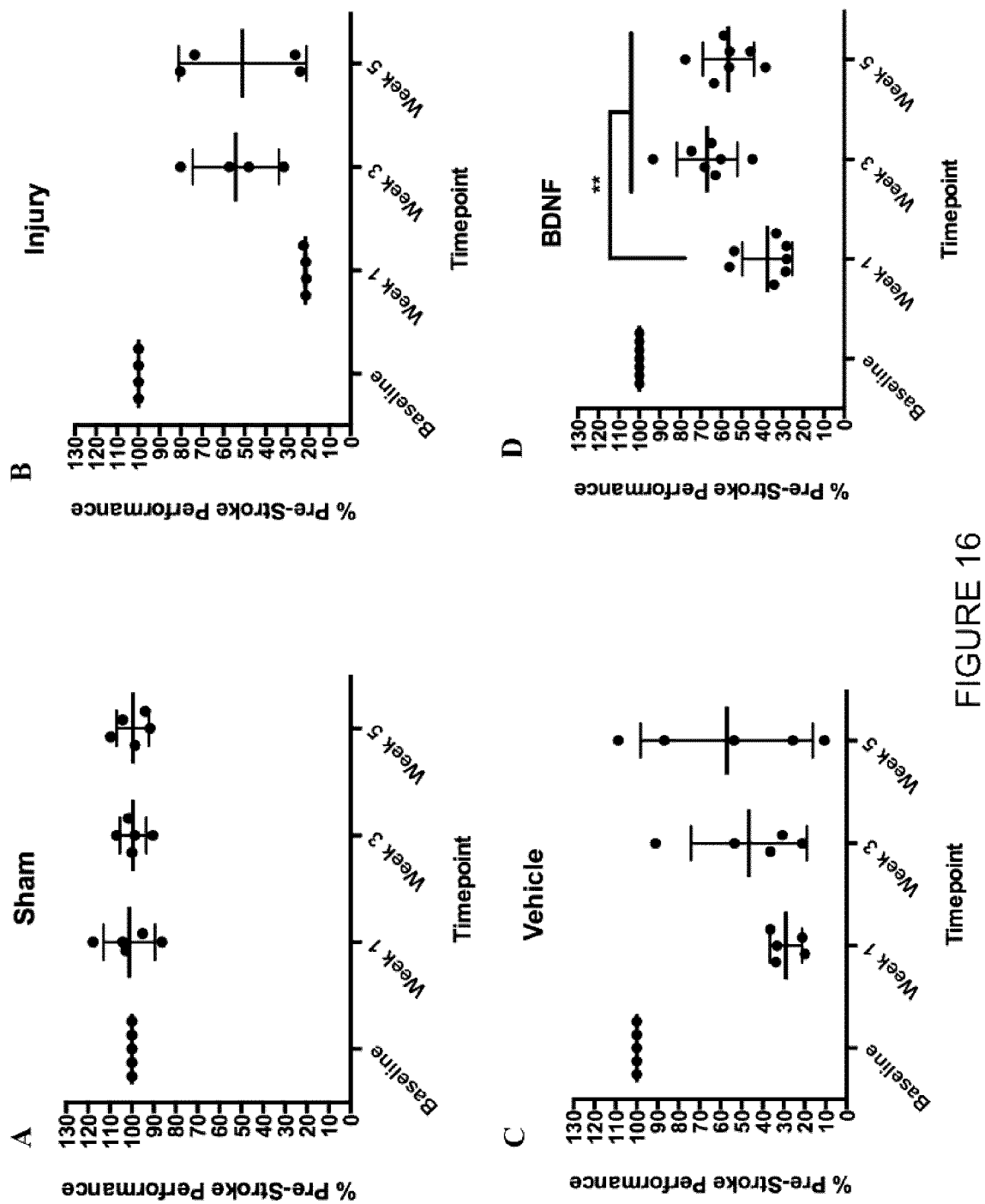
FIG. 16 shows the performance of rats in the Montoya staircase reaching task at uninjured baseline and 1, 3, and 5 weeks post-injury. Significant recovery relative to week 1 after injury was only observed in animals that received the BDNF-loaded composite, at weeks 3 and 5 post-injury (n=4, 5, 6, and 7 for sham, injury, vehicle and BDNF groups, respectively, mean±standard deviation plotted).
Figure 17:
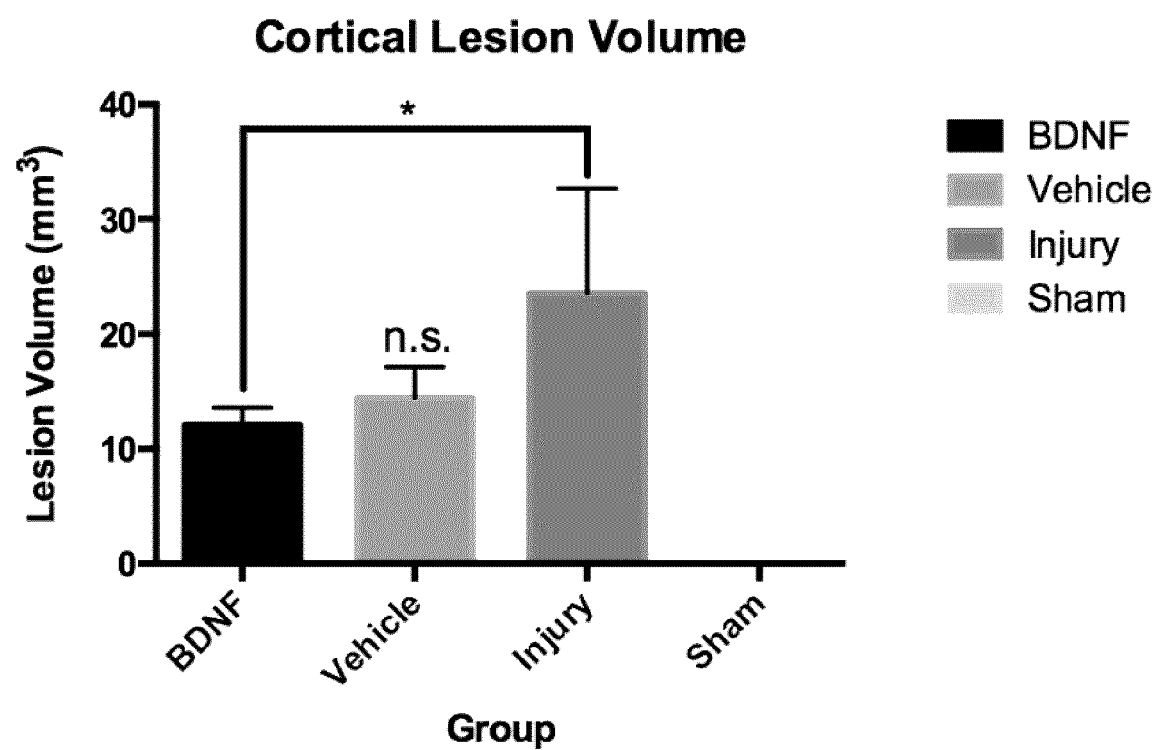
FIG. 17 shows the quantification of lesion volume in BDNF-treated, vehicle-treated, injury-only and sham animals using NeuN immunohistochemistry. A reduction in the cortical lesion volume of BDNF-treated animals relative to injury-only animals was observed (n=3 for all groups, mean±standard deviation plotted, $p^* \leq 0.05$).
Figure 18:
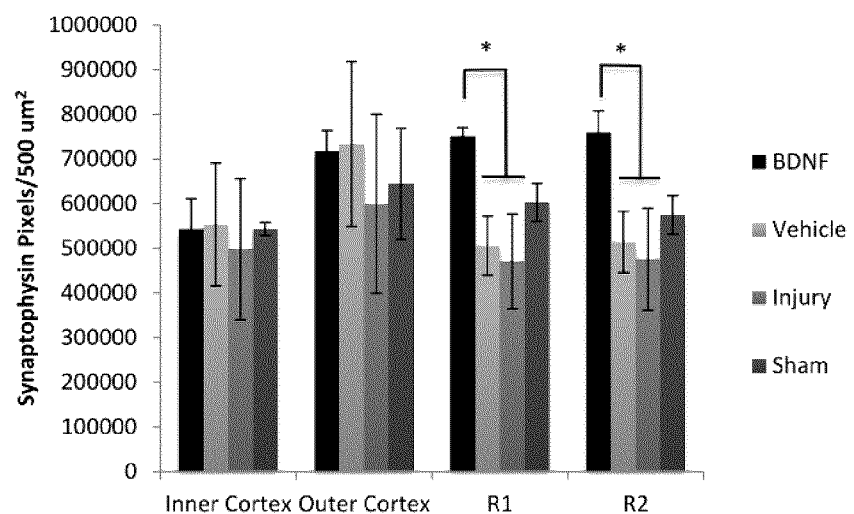
FIG. 18 shows quantification of synaptophysin staining in brain tissue regions of interest in sham, injury-only, vehicle-treated and BDNF-treated rats.
Figure 18:
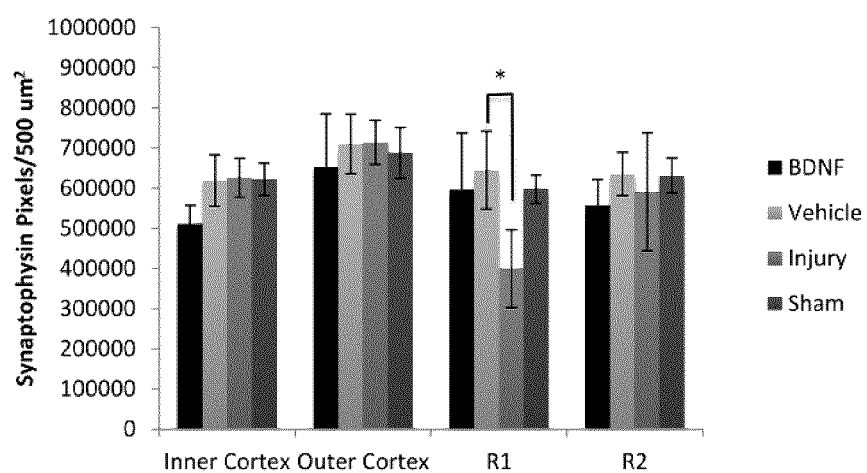

The inventors have studied multi-week release of proteins dispersed in the nanoparticle/hydrogel composite, and as can be seen from FIG. 14, in addition to the present system characterized by a delayed initial release, the present system is characterized by release, which can be sustained for at least 43 days.

The release system disclosed herein has several clinical/commercialization advantages over PLGA nanoparticle systems where the protein is encapsulated within the nanoparticle. First, with respect to sterilization, the most common method for sterilizing PLGA nanoparticles before in vivo use is terminal sterilization using gamma irradiation or electron-beam irradiation. This can be detrimental to encapsulated proteins causing oxidation, denaturation and aggregation. The present system provides controlled release without encapsulation, allowing the protein solution and the particles to be sterilized separately and then mixed together in a sterile environment prior to use. This results in a more bioactive protein available for release.

With respect to storage, PLGA nanoparticles are normally stored lyophilized which can be detrimental to protein structure and thus protein activity. By separating the particles and the protein within our delivery system we are able to store the protein under its optimal storage conditions (which may vary from protein to protein) such as frozen at −80 C, until ready for use, without reference to the PLGA nanoparticle storage conditions.

In addition, the protein encapsulation efficiency can vary between batches of protein-loaded PLGA nanoparticles. In our system, a protein solution with a known concentration is simply mixed directly into the final release system, thereby improving reproducibility. Since protein encapsulation exposes proteins to organic solvents and shear, this is also detrimental to protein activity, which is also overcome by the method and system disclosed herein.

Further, with respect to control, because the protein in the present system is separate from the PLGA nanoparticles, the protein dose can be changed without changing other system parameters. Conversely, the release rate can be tuned by changing the concentration of particles (FIG. 4Bi) without changing the therapeutic protein dose.

While the present system has been described with respect to specific examples of nanoparticle composition and proteins, it will be appreciated that the present system is not restricted to these combinations of protein and nanoparticle compositions. Specifically, the release rate of the present system can be tuned by changing the strength of the interaction or the available protein binding sites (related to total particle surface area, i.e. particle size and concentration). For a protein that is positively charged at neutral pH but with a weaker interaction than the proteins described herein, to achieve the same release profile the particle size may be decreased (effectively increasing the surface area), the particle concentration may be increased (effectively increasing the total particle surface area), or synthesize a nanoparticle with a higher net negative surface charge.

Conversely, for a protein that is positively charged at neutral pH but with a stronger interaction than the proteins described herein, to achieve the same release profile the particle sized may be increased (effectively decreasing the surface area), or the particle concentration may be decreased (effectively decreasing the total particle surface area), or synthesize a particle with a lower net negative surface charge. For a protein with a net negative charge at neutral pH, a nanoparticle with a net positive surface charge may be used. Release rate from this oppositely charged system may be tuned using particle size and concentration in the same way.

Non-limiting examples of proteins include therapeutically relevant proteins for the treatment of disease, disorder, or regenerative medicine applications. Example proteins include a growth factor, differentiation factor, antibody, chemokine, cytokine, hormone, protein vaccine, enzyme or fusion protein. In addition, the protein may be any one of nerve growth factor (NGF), erythropoietin (EPO), fibroblast growth factor (FGF), insulin-like growth factor (IGF), glial-derived neurotrophic factor (GDNF), epidermal growth factor (EGF), ciliary neurotrophic factor (CNTF), bone morphogenic protein (BMP), vascular endothelial growth factor (VEGF), stromal cell-derived factor (SDF), neurotrophin 3 (NT-3), brain-derived neurotrophic factor (BDNF), platelet-derived growth factor (PDGF), epidermal growth factor (EGF), hepatocyte growth factor (HGF), adrenomedulin (AM), angiopoietin (Ang), autocrine motility factor, leukemia inhibitory factor (LIF), interleukin-6 (IL-6), colony-stimulating factors, ephrins, fetal bovine somatotrphin (FBS), growth differentiation factor-9 (GDF9), hepatoma-derived growth factor (HDGF), insulin, interleukins, keratinocyte growth factor (KGF), migration-stimulating factor (MSF), myostatin (GDF-8), neuroregulins, placental growth factor (PGF), renalase (RNLS), T-cell growth factor (TCGF), thrombopoietin (TPO), transforming growth factors, enzymes, or antibodies.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

[1] I. Elliott Donaghue, C. H. Tator, and M. S. Shoichet, "Sustained delivery of bioactive neurotrophin-3 to the injured spinal cord," *Biomater. Sci.*, vol. 3, pp. 65-72, 2015.

[2] M. M. Pakulska, K. Vulic, R. Y. Tam, and M. S. Shoichet, "Hybrid Crosslinked Methylcellulose Hydrogel: A Predictable and Tunable Platform for Local Drug Delivery.," *Adv. Mater.*, July 2015.

[3] O. A. Hickey, J.-F. Mercier, M. G. Gauthier, F. Tessier, S. Bekhechi, and G. W. Slater, "Effective molecular diffusion coefficient in a two-phase gel medium.," *J. Chem. Phys.*, vol. 124, no. 20, p. 204903, May 2006.

[4] A. Tuladhar, C. M. Morshead, and M. S. Shoichet, "Circumventing the blood-brain barrier: Local delivery of cyclosporin A stimulates stem cells in stroke-injured rat brain," *J. Control. Release*, vol. 215, pp. 1-11, 2015.

[5] M. Singh, J. Kazzaz, J. Chesko, E. Soenawan, M. Ugozzoli, M. Giuliani, M. Pizza, R. Rappouli, and D. T. O' Hagan, "Anionic Microparticles are a Potent Delivery System for Recombinant Antigens from *Neisseria meningitidis* Serotype B," *J. Pharm. Sci.*, vol. 93, no. 2, pp. 273-282, 2004.

[6] S. K. Sahoo, J. Panyam, S. Prabha, and V. Labhasetwar, "Residual polyvinyl alcohol associated with poly (D,L-lactide-co-glycolide) nanoparticles affects their physical properties and cellular uptake," *J. Control. Release*, vol. 82, no. 1, pp. 105-114, 2002.

[7] Y. Liu and S. P. Schwendeman, "Mapping microclimate pH distribution inside protein-encapsulated PLGA microspheres using confocal laser scanning microscopy," *Mol. Pharm.*, vol. 9, no. 5, pp. 1342-1350, 2012.

[8] Y. Wang, M. J. Cooke, N. Sachewsky, C. M. Morshead, and M. S. Shoichet, "Bioengineered sequential growth factor delivery stimulates brain tissue regeneration after stroke," *J. Control. Release*, vol. 172, no. 1, pp. 1-11, 2013.

[9] C. Géral, A. Angelova, and S. Lesieur, "From Molecular to Nanotechnology Strategies for Delivery of Neurotrophins: Emphasis on Brain-Derived Neurotrophic Factor (BDNF)," *Pharmaceutics*, vol. 5, no. 1, pp. 127-167, February 2013.

Therefore what is claimed is:

1. A biocompatible polymer composite comprised of a hydrogel, proteins and nanoparticles for controlled protein release, said proteins are not encapsulated by said nanoparticles and interact with said nanoparticles by non-covalent short-range interactions, characterized in that said biocompatible polymer composite yields an extended protein release profile on the order of weeks, and the extended protein release profile is controlled by the non-covalent short-range interactions between said proteins and nanoparticles, and not by said hydrogel, wherein said nanoparticles are not comprised of polysaccharide.

2. A biocompatible polymer composite according to claim 1, wherein said release profile includes at least a 2 day delay in linear release.

3. A biocompatible polymer composite according to claim 1 wherein the hydrogel comprises any one of agarose, carrageenan, collagen, chitosan, alginate, gelatin, fibrin, hyaluronan, methyl cellulose, poly(ethylene glycol), poly (ethylene oxide), dextran, poly(vinyl alcohol), polypeptides, poly(N-isopropylacrylamide), poly(caprolactone), poly(urethane), poly(propylene oxide), poly(lactide-co-glycolide), poly(acrylates) and derivatives, co-polymers and physicals blends thereof.

4. A biocompatible polymer composite according to claim 1, wherein said nanoparticles are comprised of: poly(lactide-co-glycolide), poly(lactic acid), poly(glycolic acid), poly (ortho esters), poly(anhydrides), poly(amides), poly(ester amides), poly(phosphoesters), poly($\varepsilon$-caprolactone), poly (alkyl-cyanoacrylate), poly(ethylene glycol), or derivatives or co-polymers or physicals blends thereof.

5. A biocompatible polymer composite according to claim 1, wherein said proteins are therapeutically relevant proteins for the treatment of disease, disorder, or regenerative medicine applications.

6. A biocompatible polymer composite according to claim 5, wherein said protein is a growth factor, differentiation factor, antibody, chemokine, cytokine, hormone, protein vaccine, enzyme or fusion protein.

7. A biocompatible polymer composite according to claim 6, wherein said protein is any one of nerve growth factor (NGF), erythropoietin (EPO), fibroblast growth factor (FGF), insulin-like growth factor (IGF), glial-derived neurotrophic factor (GDNF), epidermal growth factor (EGF), ciliary neurotrophic factor (CNTF), bone morphogenic protein (BMP), vascular endothelial growth factor (VEGF), stromal cell-derived factor (SDF), neurotrophin 3 (NT-3), brain-derived neurotrophic factor (BDNF), platelet-derived growth factor (PDGF), epidermal growth factor (EGF), hepatocyte growth factor (HGF), adrenomedulin (AM), angiopoietin (Ang), autocrine motility factor, leukemia inhibitory factor (LIF), interleukin-6 (IL-6), colony-stimulating factors, ephrins, fetal bovine somatotrphin (FBS), growth differentiation factor-9 (GDF9), hepatoma-derived growth factor (HDGF), insulin, interleukins, keratinocyte growth factor (KGF), migration-stimulating factor (MSF), myostatin (GDF-8), neuroregulins, placental growth factor (PGF), renalase (RNLS), T-cell growth factor (TCGF), thrombopoietin (TPO), transforming growth factors, enzymes, or antibodies.

8. A biocompatible polymer composite according to claim 1, wherein said non-covalent short-range interactions occur between positively charged proteins and negatively charged particles in a neutral pH environment.

9. A biocompatible polymer composite according to claim 8, wherein protein release is initiated as the negatively charged particles degrade into products that decrease the strength of said non-covalent short-range interactions between positively charged proteins and negatively charged particles.

10. A biocompatible polymer composite according to claim 1, wherein said non-covalent short-range interactions occur between negatively charged proteins and positively charged particles in a neutral pH environment.

11. A biocompatible polymer composite according to claim 10, wherein protein release is initiated as the positively charged particles degrade into products that decrease the strength of said non-covalent short-range interactions between negatively charged proteins and positively charged particles.

12. A biocompatible polymer composite according to claim 1, wherein said nanoparticles have a diameter in a range from about 1 to 1000 nm.

13. A biocompatible polymer composite according to claim 1, having a composition of 0.1 to 20 wt % hydrogel/polymer scaffold, 10 pg/mL to 20 mg/mL protein and 0.1 to 20 wt % nanoparticles.

14. A process for producing a drug delivery system for extended protein release according to claim 1, comprising:
selecting a protein to be released over an extended period of time;
selecting a nanoparticle on the basis that it is made of a polymer-based material which has a charge complimentary to the charge on the protein such that the nanoparticle and the protein interact by short-range interactions;
producing the nanoparticles separate from the protein; and
mixing the protein and separate nanoparticles together with a hydrogel material under conditions conducive to the hydrogel forming to encapsulate the nanoparticles and the protein, wherein the extended protein release profile is controlled by the short-range interactions between said protein and nanoparticles, and not by said hydrogel, wherein said nanoparticles are not comprised of polysaccharide.

15. A method for providing controlled release of a protein, the method comprising: selecting a protein to be released over an extended period of time;

selecting a nanoparticle on the basis that it is made of a polymer-based material which has a charge complimentary to the charge on the protein such that the nanoparticle and the protein interact by non-covalent short range interactions;
producing the nanoparticles separate from the protein;
mixing the protein and separate nanoparticles together with a hydrogel material under conditions conducive to the hydrogel forming to encapsulate the nanoparticles and the protein to produce a biocompatible polymer composite; and
depositing the biocompatible polymer composite into an environment, whereupon degradation of the biocompatible polymer composite is characterized in that said biocompatible polymer composite yields an extended protein release profile on the order of weeks, and the extended protein release is controlled by the non-covalent short-range interactions between said proteins and nanoparticles, and not by said hydrogel, wherein said nanoparticles are not comprised of polysaccharide.

16. A method according to claim 15, wherein said release profile includes at least a 2 day delay in linear release.

17. A method according to claim 15 wherein the hydrogel comprises any one of agarose, carrageenan, collagen, chitosan, alginate, gelatin, fibrin, hyaluronan, methyl cellulose, poly(ethylene glycol), poly(ethylene oxide), dextran, poly(vinyl alcohol), polypeptides, poly(N-isopropylacrylamide), poly(caprolactone), poly(urethane), poly(propylene oxide), poly(lactide-co-glycolide), poly(acrylates) and derivatives, co-polymers and physicals blends thereof.

18. A method according to claim 15, wherein said nanoparticles are comprised of: poly(lactide-co-glycolide), poly(lactic acid), poly(glycolic acid), poly(ortho esters), poly(anhydrides), poly(amides), poly(ester amides), poly(phosphoesters), poly($\varepsilon$-caprolactone), poly(alkylcyanoacrylate), poly(ethylene glycol), or derivatives or co-polymers or physicals blends thereof.

19. A method according to claim 15, wherein said proteins are therapeutically relevant proteins for the treatment of disease, disorder, or regenerative medicine applications.

20. A method according to claim 19, wherein said protein is a growth factor, differentiation factor, antibody, chemokine, cytokine, hormone, protein vaccine, enzyme or fusion protein.

21. A method according to claim 20, wherein said protein is any one of nerve growth factor (NGF), erythropoietin (EPO), fibroblast growth factor (FGF), insulin-like growth factor (IGF), glial-derived neurotrophic factor (GDNF), epidermal growth factor (EGF), ciliary neurotrophic factor (CNTF), bone morphogenic protein (BMP), vascular endothelial growth factor (VEGF), stromal cell-derived factor (SDF), neurotrophin 3 (NT-3), brain-derived neurotrophic factor (BDNF), platelet-derived growth factor (PDGF), epidermal growth factor (EGF), hepatocyte growth factor (HGF), adrenomedulin (AM), angiopoietin (Ang), autocrine motility factor, leukemia inhibitory factor (LIF), interleukin-6 (IL-6), colony-stimulating factors, ephrins, fetal bovine somatotrphin (FBS), growth differentiation factor-9 (GDF9), hepatoma-derived growth factor (HDGF), insulin, interleukins, keratinocyte growth factor (KGF), migration-stimulating factor (MSF), myostatin (GDF-8), neuroregulins, placental growth factor (PGF), renalase (RNLS), T-cell growth factor (TCGF), thrombopoietin (TPO), transforming growth factors, enzymes, or antibodies.

22. A method according to claim 15, wherein non-covalent said short-range interactions occur between positively charged proteins and negatively charged particles in a neutral pH environment.

23. A method according to claim 22, wherein protein release is initiated as the negatively charged particles degrade into products that decrease the strength of said non-covalent short-range interactions between positively charged proteins and negatively charged particles.

24. A method according to claim 16, wherein said non-covalent short-range interactions occur between negatively charged proteins and positively charged particles in a neutral pH environment.

25. A method according to claim 24, wherein protein release is initiated as the positively charged particles degrade into products that decrease the strength of said non-covalent short-range interactions between negatively charged proteins and positively charged particles.

26. A method according to claim 15, wherein said nanoparticles have a diameter in a range from about 1 to 1000 nm.

27. A method according to claim 15, having a composition of 0.1 to 20 wt % hydrogel/polymer scaffold, 10 pg/mL to 20 mg/mL protein and 0.1 to 20 wt % nanoparticles.

28. A biocompatible polymer composite according to claim 1, wherein said nanoparticles do not comprise polysaccharide.

29. A method according to claim 15, wherein said nanoparticles do not comprise polysaccharide.

\* \* \* \* \*

UNITED STATES PATENT AND TRADEMARK OFFICE
CERTIFICATE OF CORRECTION

PATENT NO. : 11,213,490 B2
APPLICATION NO. : 16/097916
DATED : January 4, 2022
INVENTOR(S) : Molly Shoichet et al.

Page 1 of 1

It is certified that error appears in the above-identified patent and that said Letters Patent is hereby corrected as shown below:

In the Claims

Claim 22, Column 29 should read:
22. A method according to claim 15, wherein said non-covalent short-range interactions occur between positively charged proteins and negatively charged particles in a neutral pH environment.

Claim 24, Column 29 should read:
24. A method according to claim 15, wherein said non-covalent short-range interactions occur between negatively charged proteins and positively charged particles in a neutral pH environment.

Signed and Sealed this
Twentieth Day of June, 2023

Katherine Kelly Vidal
*Director of the United States Patent and Trademark Office*